United States Patent [19]
Lee et al.

[11] Patent Number: 5,843,735
[45] Date of Patent: Dec. 1, 1998

[54] AKLAVINONE C-11 HYDROXYLASE, GENE CODING FOR SAME, EXPRESSION VECTOR THEREFOR, AND PROCESS FOR PREPARING HYBRID ANTIBIOTICS BY USING SAID VECTOR

[75] Inventors: Jung-Joon Lee; Young-Ho Kim, both of Daejeon; Soon-Kwang Hong, Chungcheongbuk-do; Young-Soo Hong, Daejeon; Cheol-Kyu Hwang, Daejeon; Hang-Sub Kim, Daejeon, all of Rep. of Korea

[73] Assignees: Korea Institute of Science and Technology; IL Dong Pharmaceutical Co., Ltd., both of Seoul, Rep. of Korea

[21] Appl. No.: 551,211

[22] Filed: Oct. 31, 1995

[30] Foreign Application Priority Data

Feb. 3, 1995 [KR] Rep. of Korea ................. 95-1950

[51] Int. Cl.$^6$ ............... C12N 15/00; C12N 9/14; C12P 21/06; C07H 21/04
[52] U.S. Cl. ............ 435/172.1; 435/195; 435/68.1; 435/320.1; 536/232; 536/6.4
[58] Field of Search ............ 536/6.4, 232; 424/93.2, 424/93.43, 180.1, 181.1, 282.1, 94.6; 435/78, 172.1, 886, 169, 71.1, 71.2, 71.3, 252.3, 252.35, 172.3, 183, 195, 320.1, 68.1

[56] References Cited

U.S. PATENT DOCUMENTS

| | | | |
|---|---|---|---|
| 4,373,094 | 2/1983 | Oki et al. | 536/6.4 |
| 4,471,052 | 9/1984 | Mitscher et al. | 435/78 |

FOREIGN PATENT DOCUMENTS

| | | | |
|---|---|---|---|
| WO 92 16629 | 10/1992 | WIPO | C12N 15/31 |

OTHER PUBLICATIONS

Filippini et al. "*Streptomyces peucetius* daunorubicin biosynthesis gene dnrF : sequence and heterologous expression". Microbiology. vol.141, pp. 1007–1016, 1995.

Niemi et al. "Hybrid anthracycline antibiotics : production of new anthracyclines by cloned genes from *Streptomyces purpurascens* in *Streptomyces galilaeus*". Microbiology. vol. 140, pp. 1351–1358, 1994.

Hong et al. "Molecular cloning and characterization of the aklavinone 11 hydroxylase gene of *Streptomyces peucetius* subsp. *caesius* ATCC 27952". Journal of Bacteriology. vol.176, No.22, pp. 7096–7101, Nov. 1994.

Niemi et al. "Nucleotide sequences and expression of genes from *Streptomyces purpurascens* that cause the production of new anthracyclines in *Streptomyces galilaaeus*". Journal of Bacteriology. vol.177, No.10, pp. 2942–2945, May 1995.

Tanaka et al. "Chemical modification of anthracycline antibiotic". Journal of Antibiotic. vol.34, No.7, pp. 850–855, Jul. 1981.

Hwang et al. "Expression of *Streptomyces peucetius* gene for doxorubicin resistance and aklavinone 11 hydroxylase in *Streptomyces galilaeus* ATCC 31133 and productionof a hybrid aclacinomycin". Antimicrobial Agents and Chemotherapy. vol.39, No.7, pp. 1616–1621, Jul. 1995.

Yoshimoto et al. "Anthracycline antibiotic 2 hydroxyaclacinomycin". Japanes Journal of Antibiotic. vol.44, No.3, pp. 277–286, Sep. 1991.

Connors et al. "Biosynthesis of anthracyclines: enzymic conversion of aklanonic acid to aklavinone and e–rhodomycinone by anthracycline–producing streptomyces". Journal of General Microbiology. vol.136, pp. 1887–1894, 1990.

Oki Toshikazu, et al., "Production of Ninteen Anthracycline Compounds by *Streptomyces Galilaeus* MA 144–MI", J. Antibiotics, 1977, vol. XXX, No. 8, pp. 683–687.

Oki Toshikazu, et al., "Antitumor Anthracycline Antibiotics Aclacinomycin A and Analogues", J. Antibiotics, 1979, vol. XXX11, No.8, pp. 801–819.

*Primary Examiner*—Marian C. Knode
*Assistant Examiner*—Datquan Lee
*Attorney, Agent, or Firm*—Anderson, Kill & Olick, P.C.

[57] ABSTRACT

Aklavinone C-11 hydroxylase separated from Streptomyces sp.; a gene encoding same; an expression vector comprising said gene; a microorganism transformed with said vector; and a process for preparing novel hybrid anthracyclines by using said vector.

10 Claims, 19 Drawing Sheets

FIG. 3A

```
       BamHI
  1    GGA TCC CGT AGA CGA GAC CGG CCG GGA CGT TGA GGT CCA GGC CGT CCA CCG CCC      54
 55    TCG TCC CGT TGT AGA CCT TGA CGA GAC CGG ACG TTT CGA TGG CCC GTG TCG GCT     108
109    GCG TGT TCA CCT AAC GCC CCC AGT AGT CAC ATG GAG CGG ACA AAG CGT GCA CTG     162
163    TAA GTT ATT TCG GTC AAT CGG GTT CAC GTT GAG TAC CGT AGC CCC CAA TGA GGA     216
            drrAB mRNA  ←⎯⎯⎯⎯⎯                             ⎯⎯⎯→
                                                             P2

217    CAC TTC ATG GCC GCG ATG GCT TCG TTC GCC GAG CCA TTT TTC GTA CGG GGC TCC     270
271    ACC GCG CCT CGT GAC CCT TTC GAG TGG GGC GCC CGA CGC TGG GGG TGC GGC AAC     324
                                                         ⎯⎯⎯→
                                                         P1 dnrF mRNA primer 2
                                 ←⎯⎯⎯⎯⎯⎯⎯⎯⎯⎯⎯⎯⎯  ←⎯⎯⎯
325    AGA CGC CGC GAA CTC AGG AGG TTT GAG GTG GCC TTG ACG AAG CCG GAT GTC GAT     378
  1                             rbs       V   A   L   T   K   P   D   V   D         9
             primer 1
       ⎯⎯⎯⎯⎯⎯⎯⎯⎯⎯⎯⎯⎯⎯
379    GTC CTC GTG GTG GGC GGC GGT CTC GGG GGG CTG TCC ACC GCC CTG TTC CTC GCC     432
 10     V   L   V   V   G   G   G   L   G   G   L   S   T   A   L   F   L   A       27

433    CGC CGG GGG GCG CGG GTC CTG CTG GTG GAG CGG CAT GCC AGC ACC TCG GTC CTG     486
 28     R   R   G   A   R   V   L   L   V   E   R   H   A   S   T   S   V   L       45

487    CCC AAG GCG GCA GGC CAG AAC CCG CGC ACC ATG GAA CTG TTC CGC TTC GGC GGC     540
 46     P   K   A   A   G   Q   N   P   R   T   M   E   L   F   R   F   G   G       63

541    GTG GCC GAC GAG ATC CTG GCC ACG GAC GAC ATC CGC GGC GCC CAG GGC GAC TTC     594
 64     V   A   D   E   I   L   A   T   D   D   I   R   G   A   Q   G   D   F       81

595    ACC ATC AAG GTC GTG GAG CGC GTG GGC GGT CGC GTT CCT GCA CAG CTT CGC GAG     648
 82     T   I   K   V   V   E   R   V   G   G   R   V   P   A   Q   L   R   E       99

649    AGC TTC GAG GAA CTG GTC GGT GCG ACG GAA CAG TGC ACG CCC ATG CCC TGG GCG     702
100     S   F   E   E   L   V   G   A   T   E   Q   C   T   P   M   P   W   A      117

703    CTC GCT CCC CAG GAC CGG GTG GAG CCC GTC CTG GTG GCC CAC GCC GCC AAG CAC     756
118     L   A   P   Q   D   R   V   E   P   V   L   V   A   H   A   A   K   H      135

757    GGC GCG GAG ATC CGG TTC GCC ACC GAA CTG ACC TCC TTC CAG GCG GGC GAC GAC     810
136     G   A   E   I   R   F   A   T   E   L   T   S   F   Q   A   G   D   D      153
```

FIG. 3B

```
 811   GGT GTC ACG GCC CGC CTG CGC GAC CTG GGC ACG GGA GCG GAG AGC ACC GTG AGC    864
 154    G   V   T   A   R   L   R   D   L   G   T   G   A   E   S   T   V   S    171

865   GCC CGC TAC CTG GTC GCC GCC GAC GGA CCC CGC AGC GCG ATC CGG GAG AGC CTG    918
 172    A   R   Y   L   V   A   A   D   G   P   R   S   A   I   R   E   S   L    189

919   GGC ATC ACC CGG CAC GGT CAC GGC ACC CTG GCC CAC TTC ATG GGC GTC ATC TTC    972
 190    G   I   T   R   H   G   H   G   T   L   A   H   F   M   G   V   I   F    207

973   GAG GCC GAC CTC ACC GCC GTC GTA CCG CCC GGG TCC ACC GGC TGG TAC TAC CTG   1026
 208    E   A   D   L   T   A   V   V   P   P   G   S   T   G   W   Y   Y   L    225

1027   CAG CAC CCG GAC TTC ACC GGC ACG TTC GGC CCC ACC GAC CGG CCC AAC CGG CAC   1080
 226    Q   H   P   D   F   T   G   T   F   G   P   T   D   R   P   N   R   H    243

1081   ACC TTC TAC GTC CGC TAC GAC CCC GAA CGC GGC GAG AGG CCG GAG GAC TAC ACA   1134
 244    T   F   Y   V   R   Y   D   P   E   R   G   E   R   P   E   D   Y   T    261

1135   CCG CAG CGC TGC ACC GAG CTG ATC CGG CTG GCT GTC GAC GCG CCC GGG CTC GTC   1188
 262    P   Q   R   C   T   E   L   I   R   L   A   V   D   A   P   G   L   V    279

1189   CCG GAC ATC CTC GAC ATC CAG GCC TGG GAC ATG GCG GCG TAC ATC GCC GAC CGG   1242
 280    P   D   I   L   D   I   Q   A   W   D   M   A   A   Y   I   A   D   R    297

1243   TGG CGC GAA GGG CCG GTG CTG CTG GTC GGC GAT GCC GCC AAG GTC ACC CCG CCC   1296
 298    W   R   E   G   P   V   L   L   V   G   D   A   A   K   V   T   P   P    315

1297   ACC GGG GGC ATG GGC GGC AAC ACC GCC ATC GGG CAC GGG TTC GAC GTG GCC TGG   1350
 316    T   G   G   M   G   G   N   T   A   I   G   H   G   F   D   V   A   W    333

1351   AAG CTG GCC GCC GTG CTG CGC GGC GAG GCG GGC GAG CGG CTC CTC GAC AGC TAC   1404
 334    K   L   A   A   V   L   R   G   E   A   G   E   R   L   L   D   S   Y    351

1405   GGG GCG GAC GGG TCG CTC GTG TCC CGC CTC GTC GTC GAC GAG TCA CTC GCC ATC   1458
 352    G   A   D   G   S   L   V   S   R   L   V   V   D   E   S   L   A   I    369

1459   TAC GCC CAG CGC ATG GCT CCC CAC CTG CTC GGC AGC GTT CCC GAG GAA CGC GGT   1512
 370    Y   A   Q   R   M   A   P   H   L   L   G   S   V   P   E   E   R   G    387
```

FIG. 3C

| | | | | | | | | | | | | | | | | | | |
|---|---|---|---|---|---|---|---|---|---|---|---|---|---|---|---|---|---|---|
| 1513 | ACG | GCG | CAG | GTC | GTC | CTG | GGC | TTC | CGC | TAC | CGC | TCC | ACC | GCC | GTC | GCC | GCC | GAG | 1566 |
| 388 | T | A | Q | V | V | L | G | F | R | Y | R | S | T | A | V | A | A | E | 405 |

BamHI

| | | | | | | | | | | | | | | | | | | |
|---|---|---|---|---|---|---|---|---|---|---|---|---|---|---|---|---|---|---|
| 1567 | GAC | GAC | GAC | CCC | GAG | CCG | ACC | GAG | GAT | CCG | CGA | CGC | CCG | TCC | GGG | CGC | CCC | GGC | 1620 |
| 406 | D | D | D | P | E | P | T | E | D | P | R | R | P | S | G | R | P | G | 423 |

| | | | | | | | | | | | | | | | | | | |
|---|---|---|---|---|---|---|---|---|---|---|---|---|---|---|---|---|---|---|
| 1621 | TTC | CGC | GCA | CCC | CAC | GTC | TGG | ATC | GAA | CAG | GAC | GGC | ACA | CGG | CGT | TCC | ACC | GTC | 1674 |
| 424 | F | R | A | P | H | V | W | I | E | Q | D | G | T | R | R | S | T | V | 441 |

| | | | | | | | | | | | | | | | | | | |
|---|---|---|---|---|---|---|---|---|---|---|---|---|---|---|---|---|---|---|
| 1675 | GAG | TTG | TTC | GGC | GAC | TGC | TGG | GTG | CTC | CTG | GCC | GCA | CCG | GAG | GGC | GGC | GCC | TGG | 1728 |
| 442 | E | L | F | G | D | C | W | V | L | L | A | A | P | E | G | G | A | W | 459 |

| | | | | | | | | | | | | | | | | | | |
|---|---|---|---|---|---|---|---|---|---|---|---|---|---|---|---|---|---|---|
| 1729 | GGC | CAG | GCG | GCC | GCC | CGC | GCC | GCG | GCG | GAT | CTG | GGC | CTC | CGC | CTC | GAC | GTC | CAT | 1782 |
| 460 | G | Q | A | A | A | R | A | A | A | D | L | G | L | R | L | D | V | H | 477 |

| | | | | | | | | | | | | | | | | | | |
|---|---|---|---|---|---|---|---|---|---|---|---|---|---|---|---|---|---|---|
| 1783 | CTC | GTC | GGC | CGC | GAT | GTC | GCC | GCC | CCC | TCC | GGC | GAA | CTG | ACG | CGG | ACC | TAC | GGG | 1836 |
| 478 | L | V | G | R | D | V | A | A | P | S | G | E | L | T | R | T | Y | G | 495 |

| | | | | | | | | | | | | | | | | | | |
|---|---|---|---|---|---|---|---|---|---|---|---|---|---|---|---|---|---|---|
| 1837 | ATC | GGC | CGG | GCG | GGG | GCC | AGC | TTG | GTG | CGG | CCG | GAC | GGC | GTG | GTC | GCC | TGG | CGT | 1890 |
| 496 | I | G | R | A | G | A | S | L | V | R | P | D | G | V | V | A | W | R | 513 |

| | | | | | | | | | | | | | | | | | | |
|---|---|---|---|---|---|---|---|---|---|---|---|---|---|---|---|---|---|---|
| 1891 | ACG | GCA | GTA | GCG | CCG | GGA | GCG | GAG | GCC | CAG | GAC | CAG | CTG | AGC | ACC | CTG | CTC | ACC | 1944 |
| 514 | T | A | V | A | P | G | A | E | A | Q | D | Q | L | S | T | L | L | T | 531 |

| | | | | | | | | | | | | | | | | | | |
|---|---|---|---|---|---|---|---|---|---|---|---|---|---|---|---|---|---|---|
| 1945 | CGG | CTG | CTG | GCC | CGC | TGA | CCG | GAG | CGT | CCC | GCG | TCG | GCG | GGG | CCA | CCA | CGG | AGC | 1998 |
| 532 | R | L | L | A | R | * | | | | | | | | | | | | | 537 |

| | | | | | | | | | | | | | |
|---|---|---|---|---|---|---|---|---|---|---|---|---|---|
| 1999 | GGT | CCG | CGC | CCG | GCG | ACG | GGG | CTC | GGG | CCA | GCC | GGC | TCC | GAC | AAC | TCC | TGT | ATG | 2052 |
| 2053 | TAA | TGA | ATC | AGT | TCA | GGC | GGC | TCG | TGC | ACC | TCG | AAC | TCG | ACG | CCG | AAG | ATC | CCG | 2106 |
| 2107 | ATG | GTG | AGC | GCC | AGC | CAC | TCC | AGC | GAG | TCG | GCG | GCC | GAA | CGC | AGC | GGC | ATG | TCC | 2160 |
| 2161 | GGT | GGT | CGA | CCG | CTG | TGA | GGA | TTC | CGT | CGC | GCG | GGC | GGA | TCC | | | | | 2202 |

BamHI

FIG. 5
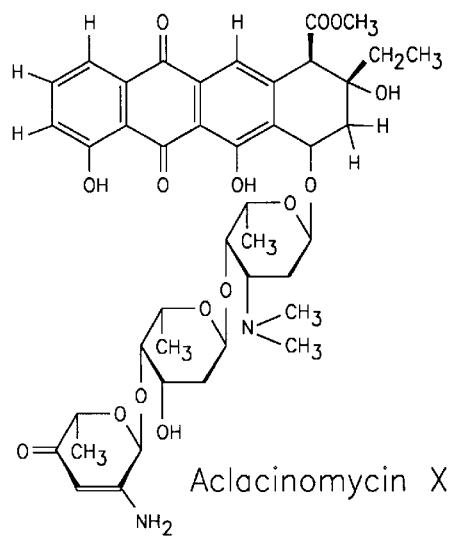
Aclacinomycin X
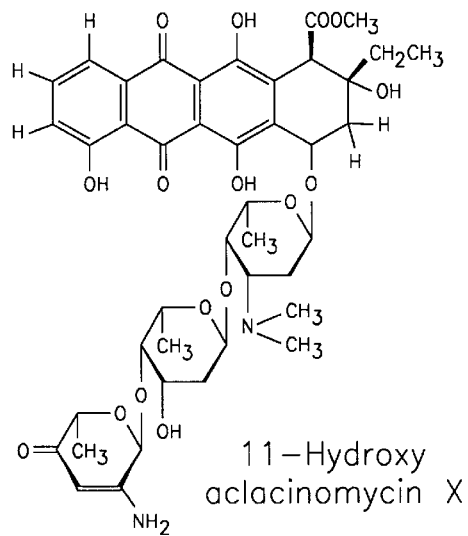
11-Hydroxy aclacinomycin X
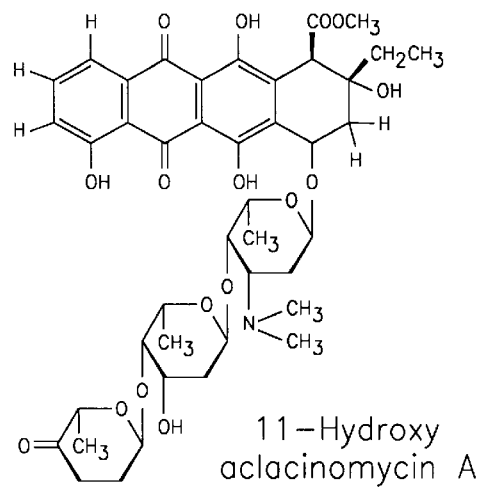
11-Hydroxy aclacinomycin A
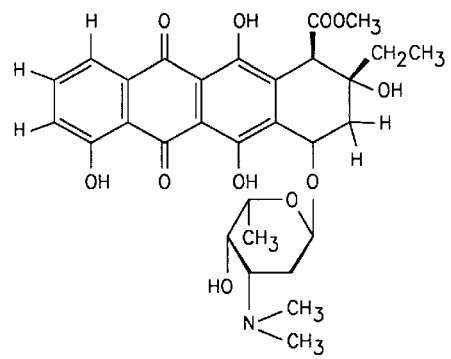
11-Hydroxy aclacinomycin T
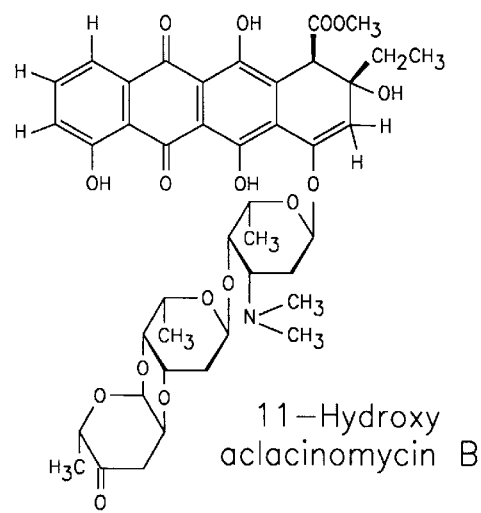
11-Hydroxy aclacinomycin B

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: primer DNA ( i i i ) ANTI-SENSE: no ( i v ) SEQUENCE DESCRIPTION: SEQ ID NO: 1:

G A G A C C G C C G    C C C A C C A C G A    G G A C A T C G A C    3 0

( 2 ) INFORMATION FOR SEQ ID NO:2:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: primer DNA (iii) ANTI-SENSE: no (iv) SEQUENCE DESCRIPTION: SEQ ID NO: 2:

ATCGACATCC GGCTTCGTCA AGGCCACCTC    30

(2) INFORMATION FOR SEQ ID NO:3:

(i) SEQUENCE CHARACTERISTICS:
(A) LENGTH: 536 amino acids
(B) TYPE: amino acid
(C) STRANDEDNESS: single
(D) TOPOLOGY: linear (ii) MOLECULE TYPE: protein (iv) SEQUENCE DESCRIPTION: SEQ ID NO: 3:

| Val | Ala | Leu | Thr | Lys | Pro | Asp | Val | Asp | Val | Leu | Val | Val | Gly | Gly |
|---|---|---|---|---|---|---|---|---|---|---|---|---|---|---|
| 1 | | | | 5 | | | | | 10 | | | | | 15 |
| Gly | Leu | Gly | Gly | Leu | Ser | Thr | Ala | Leu | Phe | Leu | Ala | Arg | Arg | Gly |
| | | | | 20 | | | | | 25 | | | | | 30 |
| Ala | Arg | Val | Leu | Leu | Val | Glu | Arg | His | Ala | Ser | Thr | Ser | Val | Leu |
| | | | | 35 | | | | | 40 | | | | | 45 |
| Pro | Lys | Ala | Ala | Gly | Gln | Asn | Pro | Arg | Thr | Met | Glu | Leu | Phe | Arg |
| | | | | 50 | | | | | 55 | | | | | 60 |
| Phe | Gly | Gly | Val | Ala | Asp | Glu | Ile | Leu | Ala | Thr | Asp | Asp | Ile | Arg |
| | | | | 65 | | | | | 70 | | | | | 75 |
| Gly | Ala | Gln | Gly | Asp | Phe | Thr | Ile | Lys | Val | Val | Glu | Arg | Val | Gly |
| | | | | 80 | | | | | 85 | | | | | 90 |
| Gly | Arg | Val | Pro | Ala | Gln | Leu | Arg | Glu | Ser | Phe | Glu | Glu | Leu | Val |
| | | | | 95 | | | | | 100 | | | | | 105 |
| Gly | Ala | Thr | Glu | Gln | Cys | Thr | Pro | Met | Pro | Trp | Ala | Leu | Ala | Pro |
| | | | | 110 | | | | | 115 | | | | | 120 |
| Gln | Asp | Arg | Val | Glu | Pro | Val | Leu | Val | Ala | His | Ala | Ala | Lys | His |
| | | | | 125 | | | | | 130 | | | | | 135 |
| Gly | Ala | Glu | Ile | Arg | Phe | Ala | Thr | Glu | Leu | Thr | Ser | Phe | Gln | Ala |
| | | | | 140 | | | | | 145 | | | | | 150 |
| Gly | Asp | Asp | Gly | Val | Thr | Ala | Arg | Leu | Arg | Asp | Leu | Gly | Thr | Gly |
| | | | | 155 | | | | | 160 | | | | | 165 |
| Ala | Glu | Ser | Thr | Val | Ser | Ala | Arg | Tyr | Leu | Val | Ala | Ala | Asp | Gly |
| | | | | 170 | | | | | 175 | | | | | 180 |
| Pro | Arg | Ser | Ala | Ile | Arg | Glu | Ser | Leu | Gly | Ile | Thr | Arg | His | Gly |
| | | | | 185 | | | | | 190 | | | | | 195 |
| His | Gly | Thr | Leu | Ala | His | Phe | Met | Gly | Val | Ile | Phe | Glu | Ala | Asp |
| | | | | 200 | | | | | 205 | | | | | 210 |
| Leu | Thr | Ala | Val | Val | Pro | Pro | Gly | Ser | Thr | Gly | Trp | Tyr | Tyr | Leu |
| | | | | 215 | | | | | 220 | | | | | 225 |
| Gln | His | Pro | Asp | Phe | Thr | Gly | Thr | Phe | Gly | Pro | Thr | Asp | Arg | Pro |
| | | | | 230 | | | | | 235 | | | | | 240 |
| Asn | Arg | His | Thr | Phe | Tyr | Val | Arg | Tyr | Asp | Pro | Glu | Arg | Gly | Glu |
| | | | | 245 | | | | | 250 | | | | | 255 |
| Arg | Pro | Glu | Asp | Tyr | Thr | Pro | Gln | Arg | Cys | Thr | Glu | Leu | Ile | Arg |
| | | | | 260 | | | | | 265 | | | | | 270 |
| Leu | Ala | Val | Asp | Ala | Pro | Gly | Leu | Val | Pro | Asp | Ile | Leu | Asp | Ile |
| | | | | 275 | | | | | 280 | | | | | 285 |
| Gln | Ala | Trp | Asp | Met | Ala | Ala | Tyr | Ile | Ala | Asp | Arg | Trp | Arg | Glu |
| | | | | 290 | | | | | 295 | | | | | 300 |

```
       Gly  Pro  Val  Leu  Leu  Val  Gly  Asp  Ala  Ala  Lys  Val  Thr  Pro  Pro
                           305                      310                      315

Thr  Gly  Gly  Met  Gly  Gly  Asn  Thr  Ala  Ile  Gly  His  Gly  Phe  Asp
                           320                      325                      330

Val  Ala  Trp  Lys  Leu  Ala  Ala  Val  Leu  Arg  Gly  Glu  Ala  Gly  Glu
                           335                      340                      345

Arg  Leu  Leu  Asp  Ser  Tyr  Gly  Ala  Asp  Gly  Ser  Leu  Val  Ser  Arg
                           350                      355                      360

Leu  Val  Val  Asp  Glu  Ser  Leu  Ala  Ile  Tyr  Ala  Gln  Arg  Met  Ala
                           365                      370                      375

Pro  His  Leu  Leu  Gly  Ser  Val  Pro  Glu  Glu  Arg  Gly  Thr  Ala  Gln
                           380                      385                      390

Val  Val  Leu  Gly  Phe  Arg  Tyr  Arg  Ser  Thr  Ala  Val  Ala  Ala  Glu
                           395                      400                      405

Asp  Asp  Asp  Pro  Glu  Pro  Thr  Glu  Asp  Pro  Arg  Arg  Pro  Ser  Gly
                           410                      415                      420

Arg  Pro  Gly  Phe  Arg  Ala  Pro  His  Val  Trp  Ile  Glu  Gln  Asp  Gly
                           425                      430                      435

Thr  Arg  Arg  Ser  Thr  Val  Glu  Leu  Phe  Gly  Asp  Cys  Trp  Val  Leu
                           440                      445                      450

Leu  Ala  Ala  Pro  Glu  Gly  Gly  Ala  Trp  Gly  Gln  Ala  Ala  Ala  Arg
                           455                      460                      465

Ala  Ala  Ala  Asp  Leu  Gly  Leu  Arg  Leu  Asp  Val  His  Leu  Val  Gly
                           470                      475                      480

Arg  Asp  Val  Ala  Ala  Pro  Ser  Gly  Glu  Leu  Thr  Arg  Thr  Tyr  Gly
                           485                      490                      495

Ile  Gly  Arg  Ala  Gly  Ala  Ser  Leu  Val  Arg  Pro  Asp  Gly  Val  Val
                           500                      505                      510

Ala  Trp  Arg  Thr  Ala  Val  Ala  Pro  Gly  Ala  Glu  Ala  Gln  Asp  Gln
                           515                      520                      525

Leu  Ser  Thr  Leu  Leu  Thr  Arg  Leu  Leu  Ala  Arg
                           530                      535
```

( 2 ) INFORMATION FOR SEQ ID NO:4:

( i ) SEQUENCE CHARACTERISTICS:
        ( A ) LENGTH: 1611 bases
        ( B ) TYPE: nucleic acid
        ( C ) STRANDEDNESS: single
        ( D ) TOPOLOGY: linear ( i i ) MOLECULE TYPE: DNA ( i i i ) ANTI-SENSE: no ( v ) SEQUENCE DESCRIPTION: SEQ ID NO: 4:

```
GTGGCCTTGA  CGAAGCCGGA  TGTCGATGTC  CTCGTGGTGG  GCGGCGGTCT  CGGGGGGCTG      60

TCCACCGCCC  TGTTCCTCGC  CCGCCGGGGG  GCGCGGGTCC  TGCTGGTGGA  GCGGCATGCC     120

AGCACCTCGG  TCCTGCCCAA  GGCGGCAGGC  CAGAACCCGC  GCACCATGGA  ACTGTTCCGC     180

TTCGGCGGCG  TGGCCGACGA  GATCCTGGCC  ACGGACGACA  TCCGCGGCGC  CCAGGGCGAC     240

TTCACCATCA  AGGTCGTGGA  GCGCGTGGGC  GGTCGCGTTC  CTGCACAGCT  TCGCGAGAGC     300

TTCGAGGAAC  TGGTCGGTGC  GACGGAACAG  TGCACGCCCA  TGCCCTGGGC  GCTCGCTCCC     360

CAGGACCGGG  TGGAGCCCGT  CCTGGTGGCC  CACGCCGCCA  GCACGGCGC   GGAGATCCGG     420

TTCGCCACCG  AACTGACCTC  CTTCCAGGCG  GGCGACGACG  GTGTCACGGC  CCGCCTGCGC     480

GACCTGGGCA  CGGGAGCGGA  GAGCACCGTG  AGCGCCCGCT  ACCTGGTCGC  CGCCGACGGA     540
```

-continued

```
CCCCGCAGCG CGATCCGGGA GAGCCTGGGC ATCACCCGGC ACGGTCACGG CACCCTGGCC    600
CACTTCATGG GCGTCATCTT CGAGGCCGAC CTCACCGCCG TCGTACCGCC CGGGTCCACC    660
GGCTGGTACT ACCTGCAGCA CCCGGACTTC ACCGGCACGT TCGGCCCCAC CGACCGGCCC    720
AACCGGCACA CCTTCTACGT CCGCTACGAC CCCGAACGCG GCGAGAGGCC GGAGGACTAC    780
ACACCGCAGC GCTGCACCGA GCTGATCCGG CTGGCTGTCG ACGCGCCCGG GCTCGTCCCG    840
GACATCCTCG ACATCCAGGC CTGGGACATG GCGGCGTACA TCGCCGACCG GTGGCGCGAA    900
GGGCCGGTGC TGCTGGTCGG CGATGCCGCC AAGGTCACCC CGCCCACCGG GGCATGGGC    960
GGCAACACCG CCATCGGGCA CGGGTTCGAC GTGGCCTGGA AGCTGGCCGC CGTGCTGCGC   1020
GGCGAGGCGG GCGAGCGGCT CCTCGACAGC TACGGGGCGG ACGGGTCGCT CGTGTCCCGC   1080
CTCGTCGTCG ACGAGTCACT CGCCATCTAC GCCAGCGCA TGGCTCCCCA CCTGCTCGGC   1140
AGCGTTCCCG AGGAACGCGG TACGGCGCAG GTCGTCCTGG GCTTCCGCTA CCGCTCCACC   1200
GCCGTCGCCG CCGAGGACGA CGACCCCGAG CCGACCGAGG ATCCGCGACG CCCGTCCGGG   1260
CGCCCCGGCT TCCGCGCACC CCACGTCTGG ATCAACAGG ACGGCACACG GCGTTCCACC   1320
GTCGAGTTGT TCGGCGACTG CTGGGTGCTC CTGGCCGCAC CGGAGGGCGG CGCCTGGGGC   1380
CAGGCGGCCG CCCGCGCCGC GGCGGATCTG GGCCTCCGCC TCGACGTCCA TCTCGTCGGC   1440
CGCGATGTCG CCGCCCCCTC CGGCGAACTG ACGCGGACCT ACGGGATCGG CCGGGCGGGG   1500
GCCAGCTTGG TGCGGCCGGA CGGCGTGGTC GCCTGGCGTA CGGCAGTAGC GCCGGGAGCG   1560
GAGGCCCAGG ACCAGCTGAG CACCCTGCTC ACCCGGCTGC TGGCCCGCTG A            1611
```

( 2 ) INFORMATION FOR SEQ ID NO:5:

( i ) SEQUENCE CHARACTERISTICS:
        ( A ) LENGTH: 2202 bases
        ( B ) TYPE: nucleic acid
        ( C ) STRANDEDNESS: single
        ( D ) TOPOLOGY: linear ( i i ) MOLECULE TYPE: DNA ( i i i ) ANTI-SENSE: no ( i v ) FEATURE: from 340 to 345bp ribosome binding site
              from 352 to 1959bp coding sequence
              from 1960 to 1962bp terminator ( i v ) SEQUENCE DESCRIPTION: SEQ ID NO: 5:

```
GGATCCCGTA GACGAGACCG GCCGGGACGT TGAGGTCCAG GCCGTCCACC GCCCTCGTCC     60
CGTTGTAGAC CTTGACGAGA CCGGACGTTT CGATGGCCCG TGTCGGCTGC GTGTTCACCT    120
AACGCCCCCA GTAGTCACAT GGAGCGGACA AAGCGTGCAC TGTAAGTTAT TTCGGTCAAT    180
CGGGTTCACG TTGAGTACCG TAGCCCCCAA TGAGGACACT TCATGGCCGC GATGGCTTCG    240
TTCGCCGAGC CATTTTTCGT ACGGGGCTCC ACCGCGCCTC GTGACCCTTT CGAGTGGGGC    300
GCCCGACGCT GGGGGTGCGG CAACAGACGC CGCGAACTCA GGAGGTTTGA G             351

GTG GCC TTG ACG AAG CCG GAT GTC GAT GTC CTC GTG GTG GGC GGC GGT     399
Val Ala Leu Thr Lys Pro Asp Val Asp Val Leu Val Val Gly Gly Gly
 1               5                  10                  15

CTC GGG GGG CTG TCC ACC GCC CTG TTC CTC GCC CGC CGG GGC GCG CGG     447
Leu Gly Gly Leu Ser Thr Ala Leu Phe Leu Ala Arg Arg Gly Ala Arg
             20                  25                  30

GTC CTG CTG GTG GAG CGG CAT GCC AGC ACC TCG GTC CTG CCC AAG GCG     495
Val Leu Leu Val Glu Arg His Ala Ser Thr Ser Val Leu Pro Lys Ala
         35                  40                  45
```

```
GCA  GGC  CAG  AAC  CCG  CGC  ACC  ATG  GAA  CTG  TTC  CGC  TTC  GGC  GGC  GTG     543
Ala  Gly  Gln  Asn  Pro  Arg  Thr  Met  Glu  Leu  Phe  Arg  Phe  Gly  Gly  Val
     50                  55                       60

GCC  GAC  GAG  ATC  CTG  GCC  ACG  GAC  GAC  ATC  CGC  GGC  GCC  CAG  GGC  GAC     591
Ala  Asp  Glu  Ile  Leu  Ala  Thr  Asp  Asp  Ile  Arg  Gly  Ala  Gln  Gly  Asp
65                       70                  75                            80

TTC  ACC  ATC  AAG  GTC  GTG  GAG  CGC  GTG  GGC  GGT  CGC  GTT  CCT  GCA  CAG     639
Phe  Thr  Ile  Lys  Val  Val  Glu  Arg  Val  Gly  Gly  Arg  Val  Pro  Ala  Gln
                    85                       90                       95

CTT  CGC  GAG  AGC  TTC  GAG  GAA  CTG  GTC  GGT  GCG  ACG  GAA  CAG  TGC  ACG     687
Leu  Arg  Glu  Ser  Phe  Glu  Glu  Leu  Val  Gly  Ala  Thr  Glu  Gln  Cys  Thr
               100                      105                      110

CCC  ATG  CCC  TGG  GCG  CTC  GCT  CCC  CAG  GAC  CGG  GTG  GAG  CCC  GTC  CTG     735
Pro  Met  Pro  Trp  Ala  Leu  Ala  Pro  Gln  Asp  Arg  Val  Glu  Pro  Val  Leu
          115                      120                      125

GTG  GCC  CAC  GCC  GCC  AAG  CAC  GGC  GCG  GAG  ATC  CGG  TTC  GCC  ACC  GAA     783
Val  Ala  His  Ala  Ala  Lys  His  Gly  Ala  Glu  Ile  Arg  Phe  Ala  Thr  Glu
     130                 135                      140

CTG  ACC  TCC  TTC  CAG  GCG  GGC  GAC  GAC  GGT  GTC  ACG  GCC  CGC  CTG  CGC     831
Leu  Thr  Ser  Phe  Gln  Ala  Gly  Asp  Asp  Gly  Val  Thr  Ala  Arg  Leu  Arg
145                      150                 155                           160

GAC  CTG  GGC  ACG  GGA  GCG  GAG  AGC  ACC  GTG  AGC  GCC  CGC  TAC  CTG  GTC     879
Asp  Leu  Gly  Thr  Gly  Ala  Glu  Ser  Thr  Val  Ser  Ala  Arg  Tyr  Leu  Val
               165                      170                           175

GCC  GCC  GAC  GGA  CCC  CGC  AGC  GCG  ATC  CGG  GAG  AGC  CTG  GGC  ATC  ACC     927
Ala  Ala  Asp  Gly  Pro  Arg  Ser  Ala  Ile  Arg  Glu  Ser  Leu  Gly  Ile  Thr
               180                      185                      190

CGG  CAC  GGT  CAC  GGC  ACC  CTG  GCC  CAC  TTC  ATG  GGC  GTC  ATC  TTC  GAG     975
Arg  His  Gly  His  Gly  Thr  Leu  Ala  His  Phe  Met  Gly  Val  Ile  Phe  Glu
          195                      200                      205

GCC  GAC  CTC  ACC  GCC  GTC  GTA  CCG  CCC  GGG  TCC  ACC  GGC  TGG  TAC  TAC    1023
Ala  Asp  Leu  Thr  Ala  Val  Val  Pro  Pro  Gly  Ser  Thr  Gly  Trp  Tyr  Tyr
210                      215                      220

CTG  CAG  CAC  CCG  GAC  TTC  ACC  GGC  ACG  TTC  GGC  CCC  ACC  GAC  CGG  CCC    1071
Leu  Gln  His  Pro  Asp  Phe  Thr  Gly  Thr  Phe  Gly  Pro  Thr  Asp  Arg  Pro
225                      230                      235                      240

AAC  CGG  CAC  ACC  TTC  TAC  GTC  CGC  TAC  GAC  CCC  GAA  CGC  GGC  GAG  AGG    1119
Asn  Arg  His  Thr  Phe  Tyr  Val  Arg  Tyr  Asp  Pro  Glu  Arg  Gly  Glu  Arg
                    245                      250                           255

CCG  GAG  GAC  TAC  ACA  CCG  CAG  CGC  TGC  ACC  GAG  CTG  ATC  CGG  CTG  GCT    1167
Pro  Glu  Asp  Tyr  Thr  Pro  Gln  Arg  Cys  Thr  Glu  Leu  Ile  Arg  Leu  Ala
               260                      265                      270

GTC  GAC  GCG  CCC  GGG  CTC  GTC  CCG  GAC  ATC  CTC  GAC  ATC  CAG  GCC  TGG    1215
Val  Asp  Ala  Pro  Gly  Leu  Val  Pro  Asp  Ile  Leu  Asp  Ile  Gln  Ala  Trp
               275                      280                      285

GAC  ATG  GCG  GCG  TAC  ATC  GCC  GAC  CGG  TGG  CGC  GAA  GGG  CCG  GTG  CTG    1263
Asp  Met  Ala  Ala  Tyr  Ile  Ala  Asp  Arg  Trp  Arg  Glu  Gly  Pro  Val  Leu
          290                      295                      300

CTG  GTC  GGC  GAT  GCC  GCC  AAG  GTC  ACC  CCG  CCC  ACC  GGG  GGC  ATG  GGC    1311
Leu  Val  Gly  Asp  Ala  Ala  Lys  Val  Thr  Pro  Pro  Thr  Gly  Gly  Met  Gly
305                      310                      315                      320

GGC  AAC  ACC  GCC  ATC  GGG  CAC  GGG  TTC  GAC  GTG  GCC  TGG  AAG  CTG  GCC    1359
Gly  Asn  Thr  Ala  Ile  Gly  His  Gly  Phe  Asp  Val  Ala  Trp  Lys  Leu  Ala
                    325                      330                      335

GCC  GTG  CTG  CGC  GGC  GAG  GCG  GGC  GAG  CGG  CTC  CTC  GAC  AGC  TAC  GGG    1407
Ala  Val  Leu  Arg  Gly  Glu  Ala  Gly  Glu  Arg  Leu  Leu  Asp  Ser  Tyr  Gly
               340                      345                      350

GCG  GAC  GGG  TCG  CTC  GTG  TCC  CGC  CTC  GTC  GTC  GAC  GAG  TCA  CTC  GCC    1455
Ala  Asp  Gly  Ser  Leu  Val  Ser  Arg  Leu  Val  Val  Asp  Glu  Ser  Leu  Ala
               355                      360                      365
```

| | | | | | | | | | | | | | | | | |
|---|---|---|---|---|---|---|---|---|---|---|---|---|---|---|---|---|
| ATC | TAC | GCC | CAG | CGC | ATG | GCT | CCC | CAC | CTG | CTC | GGC | AGC | GTT | CCC | GAG | 1503 |
| Ile | Tyr 370 | Ala | Gln | Arg | Met | Ala 375 | Pro | His | Leu | Leu | Gly 380 | Ser | Val | Pro | Glu | |
| GAA | CGC | GGT | ACG | GCG | CAG | GTC | GTC | CTG | GGC | TTC | CGC | TAC | CGC | TCC | ACC | 1551 |
| Glu 385 | Arg | Gly | Thr | Ala | Gln 390 | Val | Val | Leu | Gly | Phe 395 | Arg | Tyr | Arg | Ser | Thr 400 | |
| GCC | GTC | GCC | GCC | GAG | GAC | GAC | GAC | CCC | GAG | CCG | ACC | GAG | GAT | CCG | CGA | 1599 |
| Ala | Val | Ala | Ala | Glu 405 | Asp | Asp | Asp | Pro | Glu 410 | Pro | Thr | Glu | Asp | Pro 415 | Arg | |
| CGC | CCG | TCC | GGG | CGC | CCC | GGC | TTC | CGC | GCA | CCC | CAC | GTC | TGG | ATC | GAA | 1647 |
| Arg | Pro | Ser | Gly 420 | Arg | Pro | Gly | Phe | Arg 425 | Ala | Pro | His | Val | Trp 430 | Ile | Glu | |
| CAG | GAC | GGC | ACA | CGG | CGT | TCC | ACC | GTC | GAG | TTG | TTC | GGC | GAC | TGC | TGG | 1695 |
| Gln | Asp | Gly 435 | Thr | Arg | Arg | Ser | Thr 440 | Val | Glu | Leu | Phe | Gly 445 | Asp | Cys | Trp | |
| GTG | CTC | CTG | GCC | GCA | CCG | GAG | GGC | GGC | GCC | TGG | GGC | CAG | GCG | GCC | GCC | 1743 |
| Val | Leu 450 | Leu | Ala | Ala | Pro | Glu 455 | Gly | Gly | Ala | Trp | Gly 460 | Gln | Ala | Ala | Ala | |
| CGC | GCC | GCG | GCG | GAT | CTG | GGC | CTC | CGC | CTC | GAC | GTC | CAT | CTC | GTC | GGC | 1791 |
| Arg 465 | Ala | Ala | Ala | Asp | Leu 470 | Gly | Leu | Arg | Leu | Asp 475 | Val | His | Leu | Val | Gly 480 | |
| CGC | GAT | GTC | GCC | GCC | CCC | TCC | GGC | GAA | CTG | ACG | CGG | ACC | TAC | GGG | ATC | 1839 |
| Arg | Asp | Val | Ala | Ala 485 | Pro | Ser | Gly | Glu | Leu 490 | Thr | Arg | Thr | Tyr | Gly 495 | Ile | |
| GGC | CGG | GCG | GGG | GCC | AGC | TTG | GTG | CGG | CCG | GAC | GGC | GTG | GTC | GCC | TGG | 1887 |
| Gly | Arg | Ala | Gly 500 | Ala | Ser | Leu | Val | Arg 505 | Pro | Asp | Gly | Val | Val 510 | Ala | Trp | |
| CGT | ACG | GCA | GTA | GCG | CCG | GGA | GCG | GAG | GCC | CAG | GAC | CAG | CTG | AGC | ACC | 1935 |
| Arg | Thr | Ala 515 | Val | Ala | Pro | Gly | Ala 520 | Glu | Ala | Gln | Asp | Gln 525 | Leu | Ser | Thr | |
| CTG | CTC | ACC | CGG | CTG | CTG | GCC | CGC | TGACCGGAGC | GTCCCGCGTC | | | | | | | 1979 |
| Leu | Leu 530 | Thr | Arg | Leu | Leu | Ala 535 | Arg | | | | | | | | | |
| GGCGGGGCCA | CCACGGAGCG | GTCCGCGCCC | GGCGACGGGG | CTCGGGCCAG | CCGGCTCCGA | | | | | | | | | | | 2039 |
| CAACTCCTGT | ATGTAATGAA | TCAGTTCAGG | CGGCTCGTGC | ACCTCGAACT | CGACGCCGAA | | | | | | | | | | | 2099 |
| GATCCCGATG | GTGAGCGCCA | GCCACTCCAG | CGAGTCGGCG | GCCGAACGCA | GCGGCATGTC | | | | | | | | | | | 2159 |
| CGGTGGTCGA | CCGCTGTGAG | GATTCCGTCG | CGCGGGCGGA | TCC | | | | | | | | | | | | 2202 |

AKLAVINONE C-11 HYDROXYLASE, GENE CODING FOR SAME, EXPRESSION VECTOR THEREFOR, AND PROCESS FOR PREPARING HYBRID ANTIBIOTICS BY USING SAID VECTOR

FIELD OF THE INVENTION

The present invention relates to aklavinone C-11 hydroxylase separated from Streptomyces sp.; a gene encoding same; an expression vector comprising said gene; a microorganism transformed with said vector; and a process for preparing novel hybrid anthracyclines by using said vector.

BACKGROUND OF THE INVENTION

Extraordinary cytotoxic activity of anthracyclines, e.g., doxorubicin(alias adriamycin), daunorubicin, and aclacinomycin, makes it possible to use them widely as anticancer agents. In particular, doxorubicin is very useful in antitumor chemotherapy, but its cardiotoxic nature limits its dosage and long-term use.

Therefore, there have been many attempts to develop new anthracyclines, particularly, derivatives of daunorubicin and doxorubicin, which have sufficiently low acute and chronic cardiotoxicity for oral administration. Epirubicin and idarubicin have thus been developed and commercialized.

Further, studies on the mechanism of biosynthesis of daunorubicin and doxorubicin in *Streptomyces peucetius* have contributed to identify a number of intermediates and enzymes which play key roles in the biosynthetic pathways (Connors, N. C., et al., *J. Gen. Microbiol.*, 136, 1887–1894 (1990)). In addition, a gene cluster containing the doxorubicin biosynthesis genes has been cloned, and its function and structure have been determined(Stutzman-Engwall K. J. and Hutchinson C. R., *Proc. Natl. Acad. Sci. U.S.A.*, 86, 3135–3139(1989)).

Meanwhile, aklavinone C-11 hydroxylase activities of Streptomyces sp. C5 and *S. peucetius* ATCC 29050, in biosynthesis of anthracyclines have been reported(Connors, N. C., et al., supra), and the location of the gene encoding aklavinone C-11 hydroxylase on a chromosome has also been reported(Colombo, A. L., et al., *J. Bacteriol.*, 174, 1641–1646(1992)). However, there have been no studies which report the nucleotide sequence and the organization of a gene encoding aklavinone C-11 hydroxylase, and the enzymatic activity thereof.

In this context, the present inventors have endeavored to elucidate the nucleotide sequence and the organization of the gene encoding aklavinone C-11 hydroxylase in order to use them in biosynthesis of novel hybrid anthracyclines. As a result, the present inventors have succeeded in cloning the aklavinone C-11 hydroxylase gene of *S. peucetius* subsp. *caesius* ATCC 27952; in unraveling its organization and nucleotide sequence of the gene as well as the amino acid sequence encoded therein; and producing novel hybrid anthracyclines by transforming Streptomyces sp., which has no aklavinone C-11 hydroxylase activity, with a vector comprising said gene and culturing the transformed microorganism under suitable conditions.

SUMMARY OF THE INVENTION

Accordingly, it is an object of the present invention to provide aklavinone C-11 hydroxylase and a gene encoding same.

Another object of the present invention is to provide a vector comprising said gene and a host cell transformed with said vector.

A further object of the present invention is to provide a process for the preparation of novel hybrid anthracyclines by using said vector.

BRIEF DESCRIPTION OF THE DRAWINGS

The above and other objects and features of the present invention will become apparent from the following description of the invention, when taken in conjunction with the accompanying drawings, in which:

FIG. 3 displays the nucleotide sequence of aklavinone C-11 hydroxylase gene and amino acid sequence encoded therein;

FIG. 5 illustrates the structure of aclacinomycin X and its hybrid homologues;

DETAILED DESCRIPTION OF THE INVENTION

Figure 1:
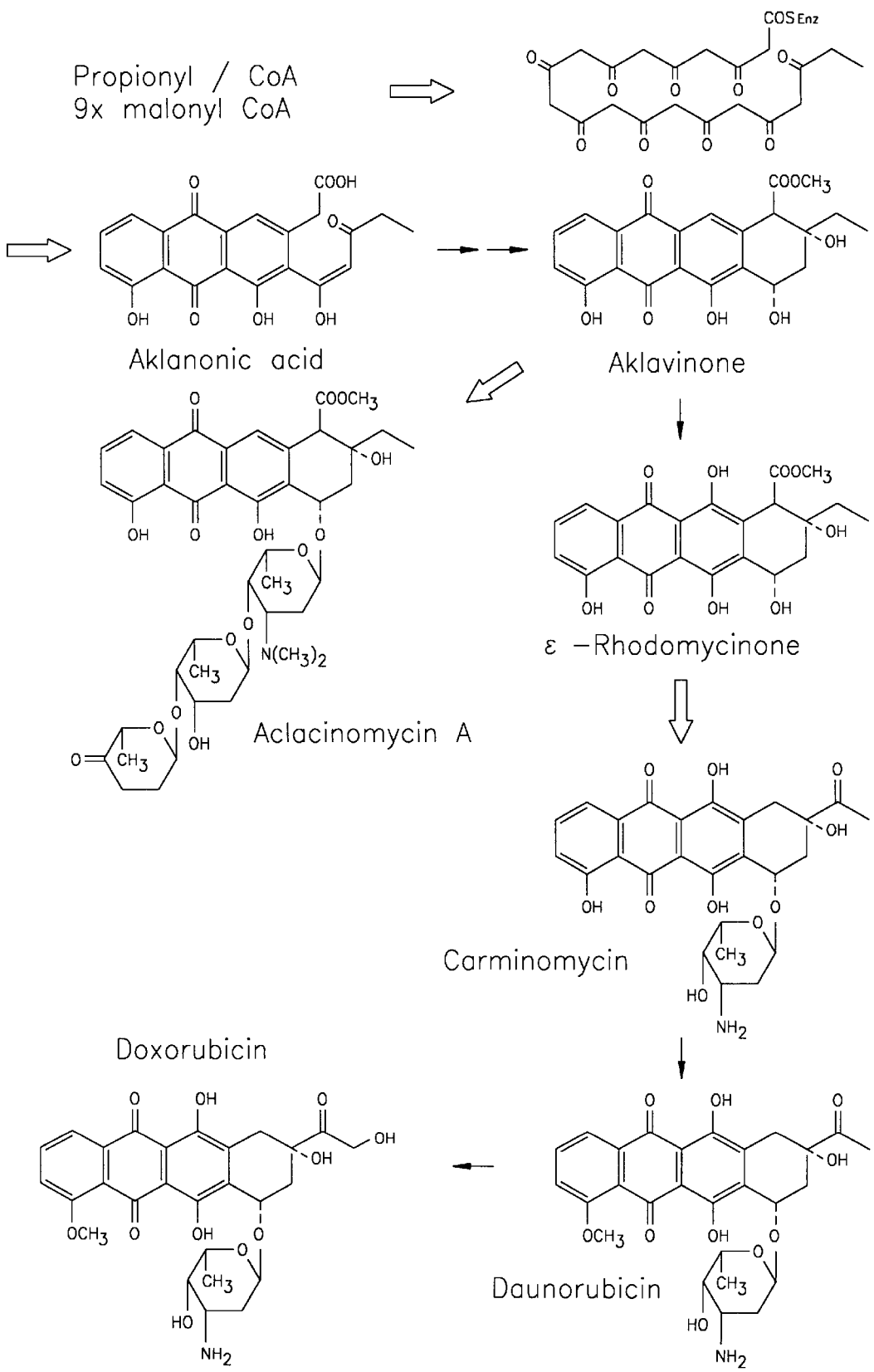
FIG. 1 shows the biosynthetic pathway of aclacinomycin and doxorubicin.

In accordance with the present invention, there is provided a gene encoding aklavinone C-11 hydroxylase, a vector comprising same and a host cell transformed with said vector.

The aklavinone C-11 hydroxylase gene of the present invention encodes aklavinone C-11 hydroxylase, which participates in the synthetic step of producing ε- rhodomycinone and daunorubicin from aklavinone, and it can be cloned from Streptomyces sp. In particular, the gene of the present invention includes the aklavinone C-11 hydroxylase gene separated from *Streptomyces peucetius* ATCC 27952 in which the protein coding region, i.e., from the 352nd to the 1962nd nucleotides, preferably comprises the nucleotide sequence disclosed in FIG. 3(SEQ ID NO: 5).

The gene of the present invention may be prepared by cloning the gene from an aklavinone C-11 hydroxylase-producing microorganism, e.g., Streptomyces sp. in accordance with a conventional method; or by chemical DNA synthesis designed on the basis of the nucleotide sequence of FIG. 3. The nucleotide sequence of the gene may be changed by substitution, deletion or addition of suitable nucleotides as long as the activity and the function of the protein encoded therein remain substantially unchanged.

Aklavinone C-11 hydroxylase of the present invention encoded by said gene has a molecular weight ranging from 57 to 58 kd and comprises the whole or a part of the amino acid sequence disclosed in FIG. 3. However, the amino acid sequence of the enzyme may also be changed by substitution, deletion or addition of suitable amino acids as long as the activity and the function of the enzyme are maintained. Aklavinone C-11 hydroxylase of the present invention may be prepared by expressing the gene encoding said enzyme in a suitable host cell, e.g., Streptomyces sp., or may be chemically synthesized in accordance with a conventional protein synthesis method.

An expression vector system may be constructed by inserting the gene encoding aklavinone C-11 hydroxylase into a vector containing a suitable expression regulating factor which is selected in accordance with the choice of a host cell. For instance, in case of using Streptomyces sp. as a host cell, a vector comprising a promoter selected from a group consisting of tipA, ermE, strR or melc1 can be employed and the examples thereof includes pKC1064 (Kuhstoss, S., et al., *Gene*, 103, 97–99(1991)); pWHM643 (Decker, H., et al., *J. Bacteriol.*, 175, 3876–3886(1993)); pTMA11(Vujaklija, D., et al., *Mol. Gen. Genet.*, 229, 119–128(1991)); and pIJ702(Katz, E., et al., *J. Gen. Microbiol.*, 129, 2703–2714(1983)). In case of using *E. coli* as a host cell, a vector comprising promoter tac or T7, e.g., plasmid pTrc or pT7 series may be employed. The aklavinone C-11 hydroxylase gene may be inserted into a vector, in an expressible state, in accordance with the conventional DNA manipulation technique.

Expression vectors prepared as above can be introduced into a suitable host cell, e.g., *Streptomyces lividans, Streptomyces peucetius, Streptomyces galilaeus*, preferably, *Streptomyces peucetius* and *Streptomyces galilaeus*, in accordance with conventional methods, e.g., the method of Hopwood(as described in *Genetic Manipulations of Streptomyces: A Laboratory Manual*, The John Innes Foundation, Norwich, United Kingdom, 1985) to obtain a transformed cell.

One of such transformed *Streptomyces lividans* strains was designated *Streptomyces lividans* 1326pMC213, deposited on Sep. 16, 1994 with the Korean Collection for Type Culture(KCTC)(Address: GERI, KIST, P.O. Box 115, Yusong, Taejon, 305–600, Republic of Korea) and then converted to a deposit under the terms of the Budapest Treaty on the International Recognition of the Deposit of Microorganism for the Purpose of Patent Procedure, on May 8, 1995 with the accession number of KCTC 0162BP.

The transformed cell is cultured under conditions that allows expression of aklavinone C-11 hydroxylase. Aklavinone C-11 hydroxylase thus produced is either separated from the host cell culture or allowed to participate directly in biosynthesis of anthracyclines in the host cell. In the latter case, it is possible to produce novel hybrid anthracyclines by using an anthracycline-producing wild-type host cell which does not show aklavinone C-11 hydroxylase activity.

Accordingly, the present invention provides a process for the preparation of novel hybrid anthracyclines which comprises the steps of: transforming a host cell which does not show aklavinone C-11 hydroxylase activity and produces an anthracycline antibiotic, with a vector comprising a gene encoding aklavinone C-11 hydroxylase; and culturing the transformed host cell to express aklavinone C-11 hydroxylase.

For instance, *Streptomyces galilaeus* producing aclacinomycin A and its homologues, which are used as anticancer agents, and lacking in aklavinone C-11 hydroxylase activity (Oki, T., et al., *J. of Antibiotics*, 32, 801–819 (1979)), is transformed with the vector of the present invention comprising a gene encoding aklavinone C-11 hydroxylase. When culturing the transformed microorganism and inducing expression of aklavinone C-11 hydroxylase, the expressed enzyme acts on aklavinone to hydroxylate it. As a result, novel hybrid aclacinomycin derivatives having a hydroxy group on the 11th carbon atom of aclacinomycin homologues, e.g., 11-hydroxy aclacinomycins A, B, G, M, S, X and Y, are produced by the transformant of wild-type *Streptomyces galilaeus*.

Further, 11-hydroxy aclacinomycin X produced in the transformed *Streptomyces galilaeus* is a novel compound, and therefore, the corresponding non-hydroxylated compound produced in the wild-type *Streptomyces galilaeus* is purified and named aclacinomycin X, which has the following structure:

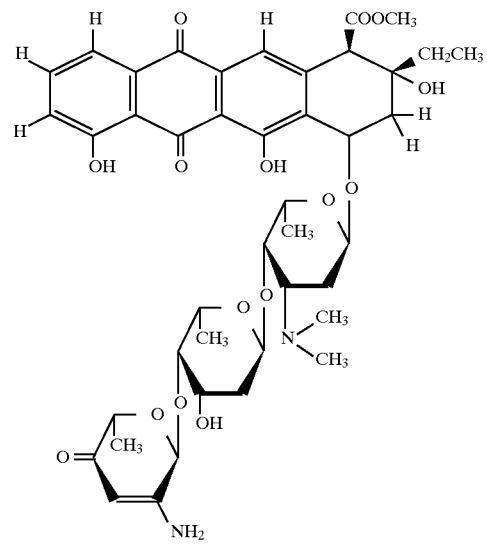

Aclacinomycin can be produced by culturing *Streptomyces galilaeus*, and then, separating and purifying it from the hyphae of *Streptomyces galilaeus* by successive extraction with acetone and chloroform, followed by silica gel column chromatography.

The hybrid anthracyclines of the present invention are expected to have properties different from those of the previously known anthracyclines. In fact, 11-hydroxy aclacinomycins A and X, and aclacinomycin X show higher growth inhibiting activities than aclacinomycin A against the various human cancer cell lines.

The following Reference Examples and Examples are intended to further illustrate the present invention without limiting its scope; and the experimental methods used in Examples are practiced in accordance with Reference Examples given hereinbelow unless otherwise stated.

Further, percentages given below for solid in solid mixture, liquid in liquid, and solid in liquid are on a wt/wt, vol/vol and wt/vol basis, respectively, unless specifically indicated otherwise.

Reference Example 1
Strains and Vectors

*Streptomyces lividans* 1326(obtained from D. A. Hopwood, John Innes Institute, Norwich, England) which produces actinorhodin was generally used in the transformation and bioconversion process for the gene cloning process, but other strains, e.g., Streptomyces peucetius ATCC 27952 which produces adriamycin, Streptomyces galilaeus ATCC 31133 which produces aclacinomycin, and Streptomyces sp. C5 which produces daunomycin and baumycin(Frederick Cancer Research Center, Frederick MD, USA) were also used for the same purposes.

The vectors used in the present invention include plasmid pIJ702 which is used exclusively in Streptomyces sp., and recombinant plasmids pMC1, pMC3, pMC4, pMC1754, pMC73 and pMC213, each having a DNA fragment encoding aklavinone C-11 hydroxylase.

Reference Example 2
Medium and Culture Conditions

R2YE agar medium was used for storing Streptomyces sp. strains and regenerating the protoplasts; R2YE or YEME liquid medium, for separating DNA or RNA and preparing protoplasts; ISP4 medium(Difco) or YS agar medium, for culturing Streptomyces sp. to form spores; and 2XYT medium, for proliferating M13 and M13KO7 phages. Streptomyces sp. harboring plasmids was selected on R2YE agar medium containing 25 µg/ml of thiostrepton, and $E.$ $coli$ with plasmids was selected on LB medium containing ampicillin(50 µg/ml), kanamycin(75 µg/ml) or apramycin (50 µg/ml). The liquid media were prepared without agar, and solid media were prepared by adding 1.5% of agar to the liquid media. Streptomyces sp. and $E.$ $coli$ were cultured at 27°–30° C. and 35°–38° C., respectively, and the culture was shaked at 250–300 rpm, unless specifically indicated otherwise.

(1) R2YE medium 103 g of sucrose, 0.25 g of $K_2SO_4$, 10 g of $MgCl_2.6H_2O$, 0.1 g of casamino acid, 5.0 g of yeast extract and 5.73 g of TES(N- tris (hydroxymethyl)methyl-2-aminoethanesulfonic acid) were dissolved in 790 ml of distilled water and the solution was sterilized. To the solution was added a sterilized mixture of 5 ml of 1M NaOH, 10 ml of 0.5% $KH_2PO_4$, 20 ml of $CaCl_2$, 15 ml of 20% proline, and 2 ml of trace element solution consisting of 40 mg of $ZnCl_2$, 200 mg of $FeCl_3.6H_2O$, 10 mg of $CuCl_2.2H_2O$, 10 mg of $MnCl_2.4H_2O$, 10 mg of $Na_2B_4O_7.10H_2O$, and 10 mg of $(NH_4)_6Mo_7O_{24}.4H_2O$ per 1 ℓ of distilled water.

(2) YEME medium 340g of sucrose, 10g of glucose, 3g of yeast extract, 5g of peptone, 3g of malt extract and 1.15g of $MgCl_2.7H_2O$ were dissolved in distilled water to adjust the total volume to 1 ℓ and the solution was sterilized before use.

(3) YS medium 3g of yeast extract and 10g of soluble starch were dissolved in 1 ℓ of distilled water, and the solution was adjusted to pH 7.2 and then sterilized before use.

(4) SGM medium 15 g of soluble starch, 10 g of glucose, 30 g of soybean flour, 1 g of yeast extract, 1 g of NaCl, 1 g of $MgSO_4$, 1 g of $KH_2PO_4$, 0.007 g of $CuSO_4$, 0.001 g of $FeSO_4$, 0.008 g of $MnCl_2$ and 0.002 g of $ZnSO_4$ were dissolved in distilled water to adjust the total volume to 1 ℓ.

(5) LB and 2XYT media

LB and 2XYT media were prepared in accordance with the method described by Maniatis et al. in *Molecular Cloning: A Laboratory Manual*, Cold Spring Harbor, N.Y., U.S.A., 1989.

Reference Example 3
Separation of Chromosomal DNA

The chromosomal DNA of $S.$ $peucetius$ subsp. $caesius$ ATCC 27952 was isolated in accordance with the method of Hunter described in *Gene Cloning in Streptomyces*, IRL Press, England, 1989.

$S.$ $peucetius$ subsp. $caesius$ ATCC 27952 was inoculated in 10 ml of R2YE agar medium and then cultured at 28° C. for 2 to 3 days. The culture was added to 100 ml of R2YE medium and then cultured to the end of logarithmic phase.

The resulting culture was centrifuged to collect the cell mass and 5g of the cell mass was suspended in 10 ml of TE buffer(10mM Tris-Cl, 1 mM EDTA, pH 8.0) containing 10 mg of lysozyme, and the reaction was allowed to proceed at 30° C. for 60 min. to disrupt the cells completely. 1 ml of 20% SDS(sodium dodecyl sulfate) was added to the suspension and the resultant was mixed gently. 1.5 ml of 5M NaCl and 10 ml of phenol were added to the mixture and the resultant mixture was shaken slowly at room temperature for 20 min.

The resulting mixture was centrifuged at 3,500 rpm for 10 min. and the supernatant was transferred to a new tube. To the tube was added same volume of chloroform and the tube was shaken gently for 10 min. The supernatant was transferred to a sterilized beaker and same volume of isopropanol was carefully added thereto. The chromosomal DNA formed in the interfacial area between the chloroform and isopropanol layers was collected with a glass rod and dissolved in a small amount of TE buffer. 20 µg/ml of RNase was added to the DNA solution and the resulting mixture was reacted at 50° C. for 1 hour. 100 µg/ml of protease K, NaCl(to a final concentration of 100 mM) and 0.4% SDS were added to the solution. The mixture was reacted at 37° C. for 1 hour, centrifuged, successively treated with chloroform and isopropanol, and then dissolved in TE buffer. The quantity of purified DNA thus obtained was calculated from the optical density (O.D.) at 260 nm.

Separation of plasmid DNA was carried out in accordance with the method of Maniatis et al. described in *Molecular Cloning: A Laboratory Manual*, Cold Spring Harbor, N.Y, U.S.A., 1989.

Reference Example 4
Separation of RNA

All of the reagents and glass tools used to separate total RNA were treated with diethylpyrocarbonate (DEPC). Microorganism cell mass obtained after culturing for 2 to 3 days was collected by centrifuge and then frozen in a dry-ice or in a liquid nitrogen vessel. The frozen cell was triturated by adding a lysis buffer solution(4M guanidium thiocyanate, 25mM sodium citrate pH 7.0, 0.5% N-lauroyl sarcosine, and 0.1M β-mercaptoethanol). The resulting solution was centrifuged using a CsCl density gradient method at 25° C., 35,000 rpm for 15 hours to separate the precipitated RNA.

Reference Example 5
Transformation of Microorganisms

The protoplasts of *Streptomyces peucetius* and *Streptomyces lividans* 1326 were prepared in accordance with a modified method based on Hopwood, supra.

Streptomyces sp. cells were inoculated in 10 ml of R2YE medium and then cultured at 28° C. for 2 to 3 days. The resulting culture was inoculated to 100 ml of R2YE medium containing 0.5% glycine and then cultured for 1 to 2 days until secondary metabolites started to emerge.

The culture was centrifuged to collect the cell mass, which was then suspended in 20 ml of P buffer(prepared in accordance with the method of Hopwood, supra) containing 1 mg/ml of lysozyme. The suspension was kept at 30° C. for 15 to 60 min., while the formation of protoplasts was examined with a microscope during the reaction. Intact cells were removed by filtering the suspension using a sterilized cotton filter and the filtered protoplasts were washed with, and suspended in, P buffer. The solution was divided by $10^{8-9}$ protoplasts and then stored at −80° C.

For use in the transformation step, the frozen protoplasts were thawed quickly at 37° C. and 1 ml of T buffer (containing 25% PEG 1000; prepared in accordance with the method of Hopwood, supra) was added thereto. Immediately thereafter, 20 µl(1 µg) of desired DNA was added to the solution, and after 1 min., the mixture was washed with 5 ml of P buffer, and dissolved in 1 ml of P buffer. The solution was then divided by 330 µl portions. Each of the fractions was mixed well with 2.5ml of R2YE medium containing 0.6% agar and then inoculated and cultured on R2YE regeneration medium. Culturing was carried out at 30° C. for 18 to 24 hours in case of *Streptomyces lividans*, and at 30° C. for 30 hours in case of *Streptomyces peucetius*. Then, 3 ml of 0.6% soft R2YE agar medium containing 25 µg/ml of thiostrepton was added to each plate and the plate was incubated at 28° C. for 3 to 5 days. The transformants were selected and analyzed for their properties.

The transformation of *E. coli* was carried out in accordance with the CaCl$_2$ method described by Maniatis, supra.

Reference Example 6
Analysis for Drug-Resistance

Streptomyces sp. was mixed with 25 ml R2YE plate medium containing doxorubicin or daunorubicin and the drug-resistance was analyzed on a square plate(100×100×15 mm) in accordance with the gradient plate method(*Science*, 116, 46–48 (1952)).

Reference Example 7
Determination of DNA Base Sequence

DNA fragments were subcloned into bacteriophages M13mpl8 and M13mp19 to obtain a single-stranded DNA. The base sequence of the DNA was determined in accordance with the dideoxy chain termination method by using [α-$^{35}$S]dATP or [α-$^{32}$P]dATP and Sequenase II or Taq polymerase(U.S. Biochemicals). For the purpose of preventing the DNA from condensation due to the high [G+C] content, the sequencing reaction was carried out at 68° C. using 7-deaza-dGTP base mixture and Taq polymerase. The synthetic oligonucleotides(consisting of 17 to 20 bases) were used as sequencing primers for determining the base sequence of the complementary DNA. The result of sequencing was analyzed by electrophoresis on 8% polyacrylamide-7M urea gel.

Reference Example 8
Analysis of Transcription Product

The size of an mRNA transcript fragment was determined by using the S1 mapping method under the condition described by Aldea, M. F., et al.(*Gene*, 65, 101–110(1988)). All transcript fragments were electrophoresed on 1% alkali agarose gel and then transferred to a nylon membrane for western blotting analysis. The fragments on the membrane protected from the action of S1 nuclease were confirmed by using a Dig-label/probe set(Boehringer Mannheim).

The transcription initiation site was determined in accordance with the primer extension method described by Guilfoile, P. G. and C. R. Hutchinson in *Proc. Natl. Acad. Sci. U.S.A.*, 88, 8553–8557(1991) and Superscript M-MLV reverse transcriptase(BRL, U.S.A.) was used in the extension reactions. Two 30-mer primers for the primer extension analysis, i.e., primer 1(5'-GAGACCGCCGCCCACCACGAGGACATCGAC-3"; SEQ ID NO:1) and primer 2(5'-ATCGACATCCGGCTTCGTCAAGGCCACCTC-3"; SEQ ID NO: 2), were designed to have nucleotide sequences complementary to the putative aklavinone C-11 hydroxylase gene (dnrF) transcript.

RNA samples were dissolved in 22 µl of DEPC-treated distilled water; then 2 µl of 10 µM primer 1 and 10 µl of 5× reverse transcriptase reaction buffer(250 mM Tris-Cl pH 8.3, 15 mM MgCl$_2$ and 375 mM KCl) were added to the solution.

The reaction mixture was kept at 75° C. for 10 min. and cooled gradually to 42° C. To the mixture were added 2 µl of dNTP mixture(10 mM dGTP, 10 mM dCTP and 10 mM dTTP), 2.5 µl of $^{35}$S-dATP(1000 Ci/mM) and 200 units of reverse transcriptase. Further, actinomycin D was added to the mixture to a final concentration of 50 µg/ml to inhibit the formation of the secondary structure of mRNA. The mixture was reacted for 30 min., followed by addition of 100 mM dATP(0.5 µl ), and then, reacted for 45 min. The presence of extended DNA was confirmed by electrophoresis on 8% polyacrylamide-7M urea gel.

Reference Example 9
Disruption of Aklavinone C-11 Hydroxylase Gene(dnrF)

An internal aklavinone C-11 hydroxylase gene fragment carrying neomycin resistance gene was inserted into plasmid pKC1139(Bierman, M. R., et al., *Gene*, 116, 43–39(1992)) to construct plasmid pKN23. Recombinant plasmid pKN23 has a temperature sensitive replicon derived from *S. ghanaensis* (Muth, G., et al., *Mol. Gen. Genet.*, 211, 4242–429 (1988)), and therefore, can be replicated at a permissive temperature, i.e., 28° C., only.

*S. peucetius* ATCC 27952 was transformed with plasmid pKN23 and the transformants were selected on R2YE plate medium containing 50 µg/ml of apramycin and 25 g/ml of neomycin and then cultured on the same medium at 28° C. for 4 days. The culture was added to R2YE liquid medium containing 50 µg/ml of apramycin and 25 µg/ml of neomycin; then cultured at a nonpermissive temperature, i.e., 39° C. for 3 days.

The culture was diluted with R2YE medium, and then, cultured on R2YE plate media containing 25 µg/ml of neomycin at 39° C. for 3 days to select the growing cells. The cells were cultured on NDYE medium(Dekleva, M. L., et al., *Can. J. Microbiol.*, 31, 287–294(1985)) for metabolite production at 28° C. to select the cells producing yellow secondary metabolite. The chromosomal DNAs of the selected cells were separated and then analyzed by southern hybridization method to confirm the disruption of dnrF gene in the chromosome.

Reference Example 10
Separation and Identification of the Metabolites

The doxorubicin and its biosynthetic intermediates produced by a microorganism were analyzed using both TLC (thin layer chromatography) and HPLC(high performance liquid chromatography).

Specifically, the microorganism cells were cultured aerobically on a production medium at 27° to 32° C. for 7 to 8 days with shaking at 250 to 300 rpm. Then, to the culture was added oxalic acid to a concentration of 30 mg/ml and hydrolysis was carried out at 55° C. for 45 min. The pH was adjusted to 8.5 by addition of 10N NaOH, and an equal volume of a chloroform : methanol(9:1) mixture was added thereto. The resultant was mixed well to extract the metabolites into the solvent layer, and then centrifuged at 3,000 rpm for 30 min. to collect the solvent layer. The obtained solvent layer was concentrated under reduced pressure and the residue was dissolved in a small amount of methanol so as to use in TLC or HPLC analyses.

TLC was carried out on a plate(silica gel 60 F-254, Merck & Co., Germany) by using a mixture of chloroform/methanol formic acid(80:20:2) as a developing solution for the glycoside intermediates and a mixture of hexanechloroform methanol(5:5:1) as a developing solution for the aglycone intermediates.

HPLC analysis was carried out on an ODS-120T C-18 column (Tosoh Co., Tokyo, Japan) using acetonitrile:20mM phosphoric acid(42:58) mixed solvent containing 10 mM SDS as an eluent.

Reference Example 11
Bioconversion Experiment

The bioconversion experiment was carried out with *Streptomyces lividans* transformants carrying plasmids pMC1 or pMC4, or other gene fragments derived from pMC1. The transformants were cultured on NDYE medium containing 25 μg/ml of thiostrepton for 2 days and 10 μg/ml of aklavinone was added to the culture. The mixture was reacted at 28° C. for 12 hours, and then extracted with chloroform methanol(9:1). The extract was dissolved in a small amount of methanol and then analyzed by TLC as described above. HPLC was carried out by using a reverse-phase ODS-120T column(Tosoh Co., Tokyo, Japan) under a linear concentration gradient of 0 to 100% acetonitrile containing 0.1% acetic acid at a flow rate of 1.5 ml/min. for 30 min.

Reference Example 12
Instrumental Analysis

An FAB-MS spectrum was obtained by using JEOL HX-110 mass spectrometer. $^1$H- and $^{13}$C-NMR spectra were obtained by using Varian UNITY-300 spectrometer and CDCl$_3$ as a solvent.

EXAMPLE 1
Cloning of Aklavinone C-11 Hydroxylase Gene(dnrF)

Chromosomal DNA of *S. peucetius* subsp. *caesius* ATCC 27952 was separated in accordance with the method of Reference Example 3 and digested partially with Sau3AI. The resulting mixture was subjected to a sucrose gradient centrifugation by using a concentration gradient of 10 to 40% sucrose to obtain 4 to 10kb DNA fragments, which were cloned into pIJ702(KCTC 1167) at Bgl II site. *S. lividans* 1326 was transformed with the resulting plasmid and then cultured successively on a R2YE agar medium containing 50 μg/ml of thiostrepton, and on a medium containing 100 μg/ml of adriamycin to selectively collect the resistant cells. The plasmids separated from the resistant cells were digested with a restriction enzyme, e.g., BamHI, SacI, KpnI or PstI.

Figure 2:
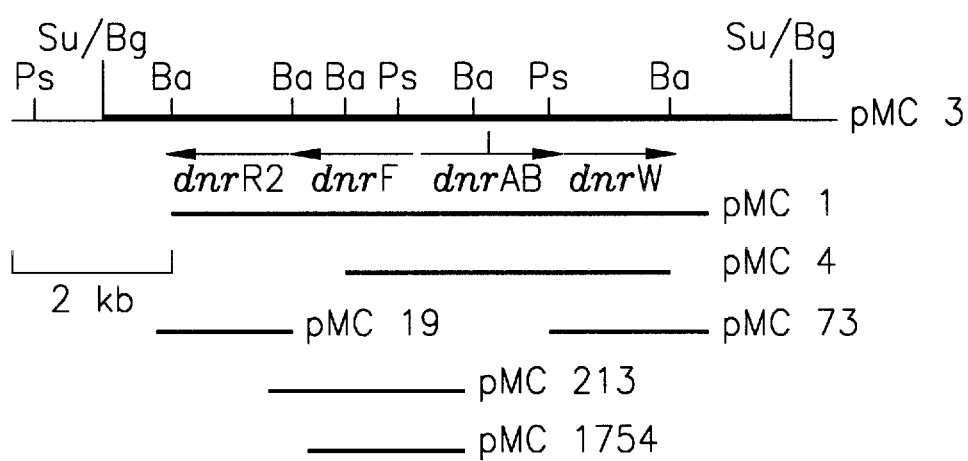
FIG. 2 depicts the restriction map of recombinant plasmids comprising aklavinone C-11 hydroxylase gene.

The size of the inserted DNA fragment was 4.4 kb for pMC4, 7.5 kb for pMC1 and 8.5 kb for pMC3, and the latter two plasmids were presumed to include the whole pMC4. The result of a southern hybridization analysis using psti 2.1 kb as a probe showed that all of the above three plasmids were hybridized with the probe(FIG.2).

In addition, subclones of pMC4 having DNA fragments smaller than 2.1 kb were prepared on the basis of the restriction map of pMC4.However, none of them showed resistance against doxorubicin. Therefore, the base sequence of 5.5 kb around the inserted DNA fragment contained in a pMC4 subclone carrying the smallest inserted DNA was analyzed, and the result showed the presence of two open reading frames (ORFS) encoding other proteins, in addition to the two resistance genes, drrA and drrB. The two ORFs found upstream and downstream from the resistance gene were named dnrF and dnrW, respectively.

The function of a gene containing dnrF was examined by introducing it to a yellow mutant F4, a mutant derived from Streptomyces sp. C5, whose biosynthetic pathway for the conversion of aklavinone to ε-rhodomycinone was blocked (Lee, J. J. et al., *Report on the Biosynthesis of Anthracyclines*, GERI, KIST, Korea, 1988). When recombinant plasmid pMC1 was introduced into mutant F4 which accumulates yellow compounds, it was observed that the mutant recovered its ability to accumulate red compounds. Further, it was confirmed by TLC and HPLC that ε-rhodomycinone was produced when aklavinone was added to the culture of *S. lividans* transformed with pMC1. The result showed that recombinant plasmid pMC1 comprises dnrF gene encoding aklavinone C-11 hydroxylase which can convert aklavinone to ε-rhodomycinone.

EXAMPLE 2
Analysis of the Nucleotide Sequence of dnrF Gene

The nucleotide sequence of 2.2 kb BamHI fragment of plasmid pMC1, which comprises a polynucleotide encoding aklavinone C-11 hydroxylase, was examined by codon preference analysis (Devereux, J. P., et al., *Nucleic Acids Res.*, 12, 387–395(1984)) to identify the coding region. As a result, about 1.6 kb of open reading frame which is expected to encode aklavinone C-11 hydroxylase and located in a direction opposite to the resistance genes(drrA and drrb) was found (FIG. 3).

The putative open reading frame for aklavinone C-11 hydroxylase has a GTG initiation codon at 352nd to 354th nucleotides and a TGA stop codon at 1960th to 1962nd nucleotides of dnrF gene. A possible ribosome binding site, i.e., GGAGG, which is complementary to the 3'-end of 16S rRNA of Streptomyces sp., was located 6bp upstream from the putative initiation codon. Further, the nucleotide sequences are located between the resistance genes and the ORF have a very high [A+T] ratio, and they are believed to play an important regulatory role in the biosynthesis of aklavinone C-11 hydroxylase as well as in the expression of the resistance genes.

The protein encoded in dnrF gene, i.e., aklavinone C-11 hydroxylase (DnrF), as deduced from nucleotide sequence, consists of 536 amino acids and has a molecular weight of about 58 kD.

EXAMPLE 3
Comparative Amino Acid Sequence Analysis of Aklavinone C-11 hydroxylase(DnrF)

The amino acid sequence of aklavinone C-11 hydroxylase (DnrF) deduced from the nucleotide sequence of dnrF was compared with those of other proteins deposited at GenBank under BLASTA and FASTA programs. It was found that the amino acid sequence of DnrF is similar to that of the flavin-type hydroxylase of bacteria such as SchC protein of *S. halsetedii* (Blanco, G., et al., *J. Bacteriology*, 175, 8043–8048(1993)) and TfdB protein of *Alcaligenes eutrophus* (Perkins, E. J., et al., *J. Bacteriology*, 172, 2351–2359 (1990)). It also showed a significant similarity with that of TcmG protein of *S. glaucescens*(Decker, H., et al., *J. Bacterioloqy*, 175, 3876–3886(1993)).

Further, the putative DnrF protein was found to contain two well-conserved amino acid sequences corresponding to the binding site for ADP moiety and the binding site for the ribityl of FAD, respectively(These binding sites generally exist in the N- and C-terminal regions of several FAD- or NAD(P)-dependent enzymes). Therefore, these hydroxylases are believed to have the same evolutionary origin, and aklavinone C-11 hydroxylase was also confirmed to be NADP-dependent.

EXAMPLE 4
Disruption of dnrF Gene in the Chromosome

For the purpose of verifying the function of aklavinone C-11 hydroxylase gene(dnrF), S. peucetius mutant strains having a disruption of dnrF gene in the chromosome were prepared in accordance with the method of Reference Example 9. The resulting mutant clones produced yellow metabolites instead of red ones produced by wild type strains, and one of the mutant clones was named PKN8.

The results of TLC and HPLC analyses of the secondary metabolites produced by wild-type S. peucetius and mutant strain PKN8 showed that the wild-type strain produces ε-rhodomycinone, carminomycin, daunorubicin and doxorubicin, while the mutant strain produces aklavinone, 11-deoxy-daunorubicin, 11-deoxycarminomycin and 11-deoxydoxorubicin. This result shows that C-11 hydroxylation of aklavinone was bypassed due to the absence of aklavinone C-11 hydroxylase activity caused by disruption of dnrF gene in the PNK8 mutant strain.

EXAMPLE 5
Expression System for Aklavinone C-11 hydroxylase

For the mass production of aklavinone C-11 hydroxylase, a highly expressible recombinant plasmid vector was constructed as follows. Plasmid pMC1 was digested partially with BamHI and subjected to an agarose gel electrophoresis to obtain a 2.2 kb DNA fragment comprising dnrF gene. The DNA fragment was inserted into BglII-digested pIJ702, which is a high copy number vector for Streptomyces sp.

Figure 4:
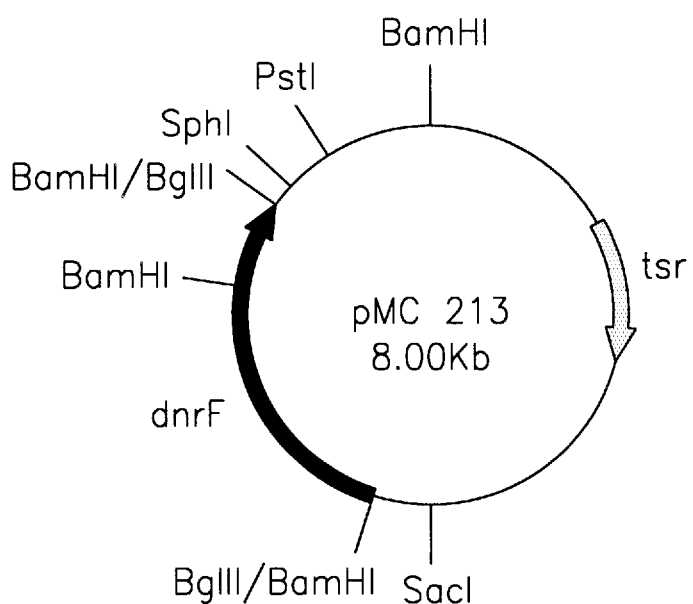
FIG. 4 exhibits the construction of plasmid pMC213.

S. lividans 1326 was transformed with the resulting recombinant plasmid, which was then separated and named pMC213(FIG. 4).

A bioconversion experiment was carried out by using a microorganism transformed with plasmid pMC213 as follows. Plasmid pMC213 was introduced into mutant strain F4 in accordance with the method of Example 1. The strain transformed with pMC213 also recovered the ability to accumulate the red metabolites as in the case of the strain transformed with pMC1, and this result shows that plasmid pMC213 comprises the dnrF gene encoding aklavinone C-11 hydroxylase.

The molecular weight of expressed aklavinone C-11 hydroxylase was 58 kD as was determined by SDS-polyacrylamide gel electrophoresis.

S. lividans carrying plasmid pMC213(S. lividans 1326/pMC213) was deposited on Sep. 16, 1994 with the Korean Collection for Type Culture(KCTC) Address: GERI, KIST, P.O. Box 115, Yusong, Taejon, 305–600, Republic of Korea) and then converted to a deposit under the terms of the Budapest Treaty on May 8, 1995 under the accession number KCTC 0162BP.

EXAMPLE 6
Transformation of S. galilaeus ATCC 31133 and Preparation of Hybrid Antibiotics S. galilaeus ATCC 31133, which produces aclacinomycin A and its homologues, was transformed with plasmid pMC213 comprising aklavinone C-11 hydroxylase gene in accordance with the method of Reference Example 5. Streptomyces galilaeus ATCC 31133 carrying plasmid pMC213 (S. galilaeus ATCC 31133pMC213) was deposited on Apr. 10, 1997 with the Korean Collection for Type Culture (KCTC)(Address: KCTC, KRIBB, #52, Oun-dong, Yusong-ku, Taejon, 305–333, Republic of Korea) under the terms of the Budapest Treaty on the International Recognition of the Deposit of Microorganism for the Purpose of Patent Procedure under the accession number of KCTC 0328BP. The transformant grown in R2YE medium was cultured in 5 ℓ of SGM production medium for 5 to 7 days, and the culture was centrifuged to obtain precipitated hyphae.

350g of hyphae was extracted with 2 ℓ of acetone at room temperature for 5 hours. The acetone extract was concentrated under vacuum and the residue was extracted with 500 ml of chloroform at room temperature for 2 hours. The chloroform extract was concentrated under a reduced pressure and the residue was dissolved in 10 ml of methanol.

The resulting solution was passed through a cartridge column filled with silica gel (XPERTEK™) and then eluted successively with chloroform and chloroform-methanol (1:1). The fractions were developed on TLC with chloroform-methanol (15:1) to collect the fractions showing Rf values similar to that of aclacinomycin A. The collected fractions were concentrated and then subjected to prep-HPLC to obtain 35 mg of a red compound, which was subsequently used in the structural analysis and in assaying its pharmaceutical effect on cancer cell lines.

In addition, the same procedure as above were repeated to separate the fractions corresponding to aclacinomycins B, M, S and Y by TLC, and the fractions, which is not corresponding to any one of those aclacinomycins, by HPLC. The purity of separated compounds was analyzed by TLC and HPLC. TLC was carried out on a silica gel plate(silica gel 60F-254, Merck, Germany) using chloroform:methanol(15:1 ) as a developing solution. HPLC was carried out by using normal phase $\mu$-porasil™ column (3.9×300 mm, Waters, U.S.A.) and chloroform-methanol-acetic acid-water(68:20:10:2) mixture containing 0.01% triethylamine as an eluent. The structures of each of the separated compounds are shown in FIG. 5.

EXAMPLE 7
Novel Antibiotic Aclacinomycin X

S. galilaeus ATCC 31133 was cultured on SGM medium at 28° C. for 3 days as a seed culture. The culture was transferred to two 5.5 ℓ fermenters containing the same medium and then cultured for 6 days as a main culture. The resulting culture was centrifuged to obtain precipitated hyphae and 400g of the hyphae was extracted twice, respectively with 2 ℓ of acetone at room temperature for 5 hours. The combined extracts were concentrated and the aqueous layer obtained therefrom was fractionated with chloroform. The chloroform layer was separated and concentrated, and then the concentrate was passed through a silica gel cartridge column using chloroform-methanol mixture with increasing the methanol concentration from 0% to 100%, and then subjected to prep-HPLC (econosil™ column (φ22.5×250 mm, Alltech), detection: UV 289 nm) using chloroform-methanol-acetic acid-water-triethylamine (68:20:10:2:0.1) at a flow rate of 8ml/min, which gave 22 mg of aclacinomycin X.

Figure 6:
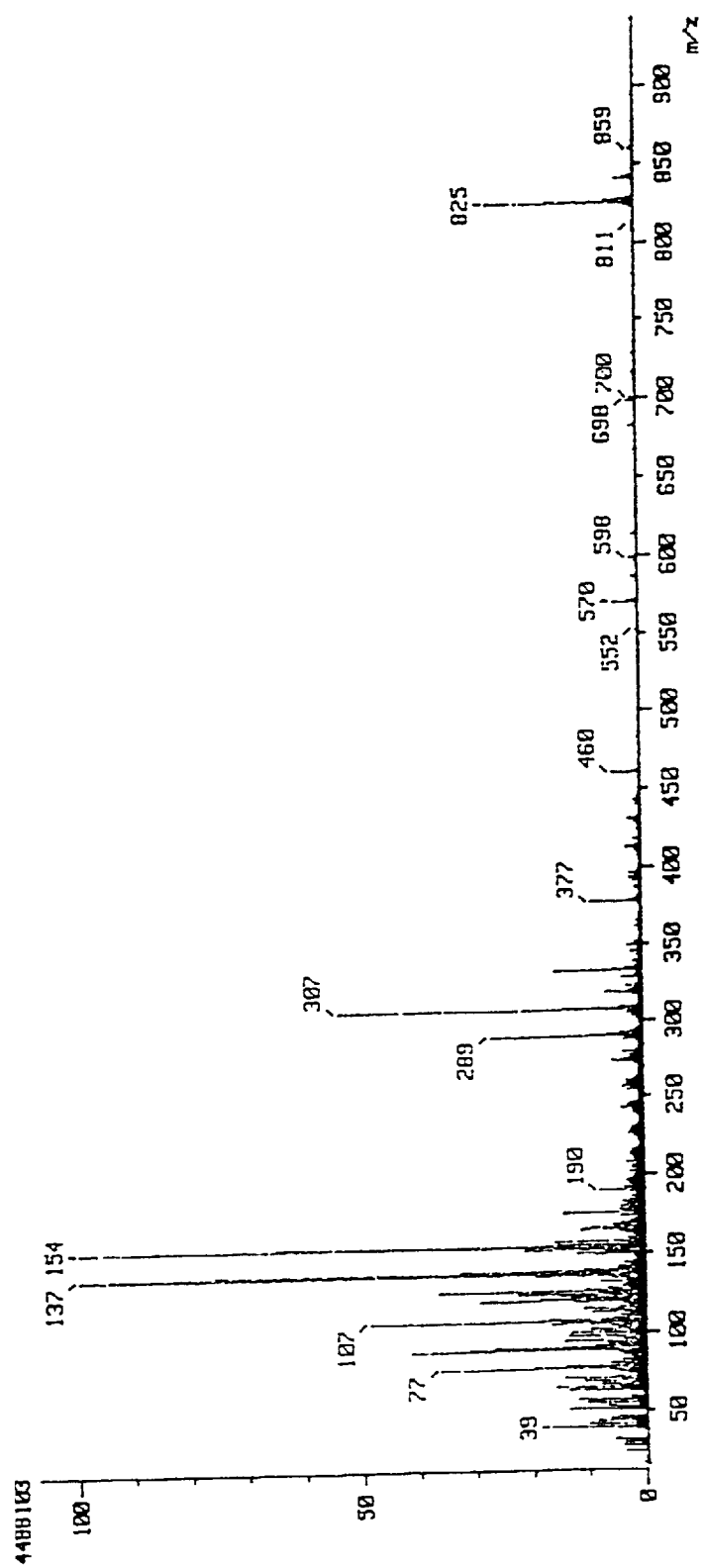
FIG. 6 shows the FAB-MS spectrum of aclacinomycin X

Aclacinomycin X is a yellow powder having a melting point of 169°–172° C., and dissolves easily in methanol or chloroform. UV spectrum of aclacinomycin X showed absorption peaks at 229, 259, 280 and 431 nm, but unlike aclacinomycin A, the absorption peak at 280 nm exhibits a hypsochromic effect. FAB-MS spectrum of aclacinomycin X showed a molecular ion peak at m/z 825 (M+H$^+$) (FIG. 6). The molecular formula of aclacinomycin X was determined as $C_{42}H_{52}N_2O_{15}$ from the M+H$^+$value of 825.3446 which was calculated based on HRFAB-MS measurements.

In the $^1$H-NMR spectrum, the aglycon moiety as well as the rhodosamine and 2-deoxy-L-fucose moieties showed the same chemical shift as aclacinomycin A, while the chemical shift of the third bound sugar residue was significantly different from that of aclacinomycin A, e.g., a new singlet peak was observed in the olefinic proton region at 5.31 ppm.

In the $^{13}$C-NMR spectrum, a quaternary carbon was observed at 163.62 ppm and a tertiary carbon, at 94.47 ppm.

Figure 7:
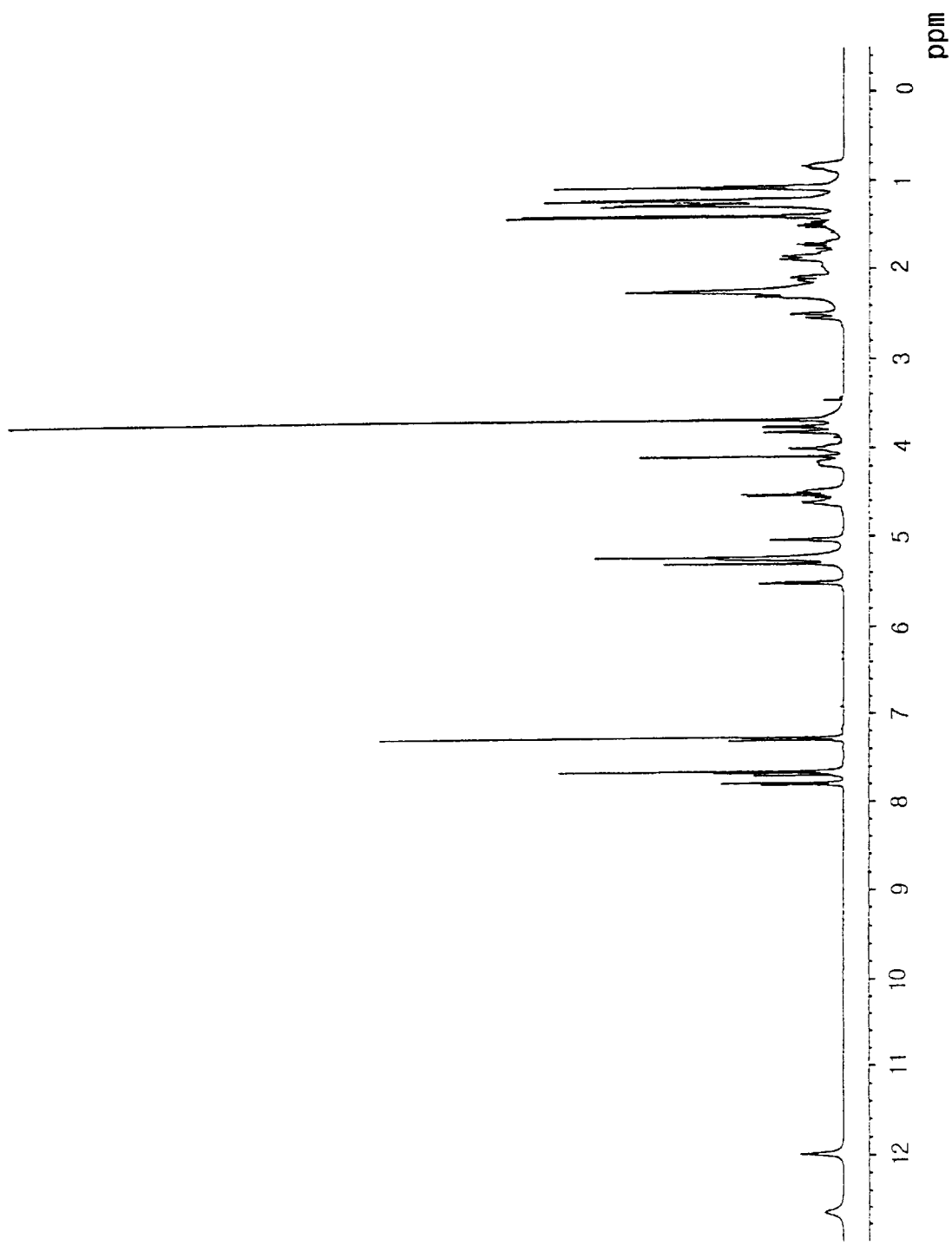
FIG. 7 depicts the $^1$H-NMR spectrum of aclacinomycin X.
Figure 8:
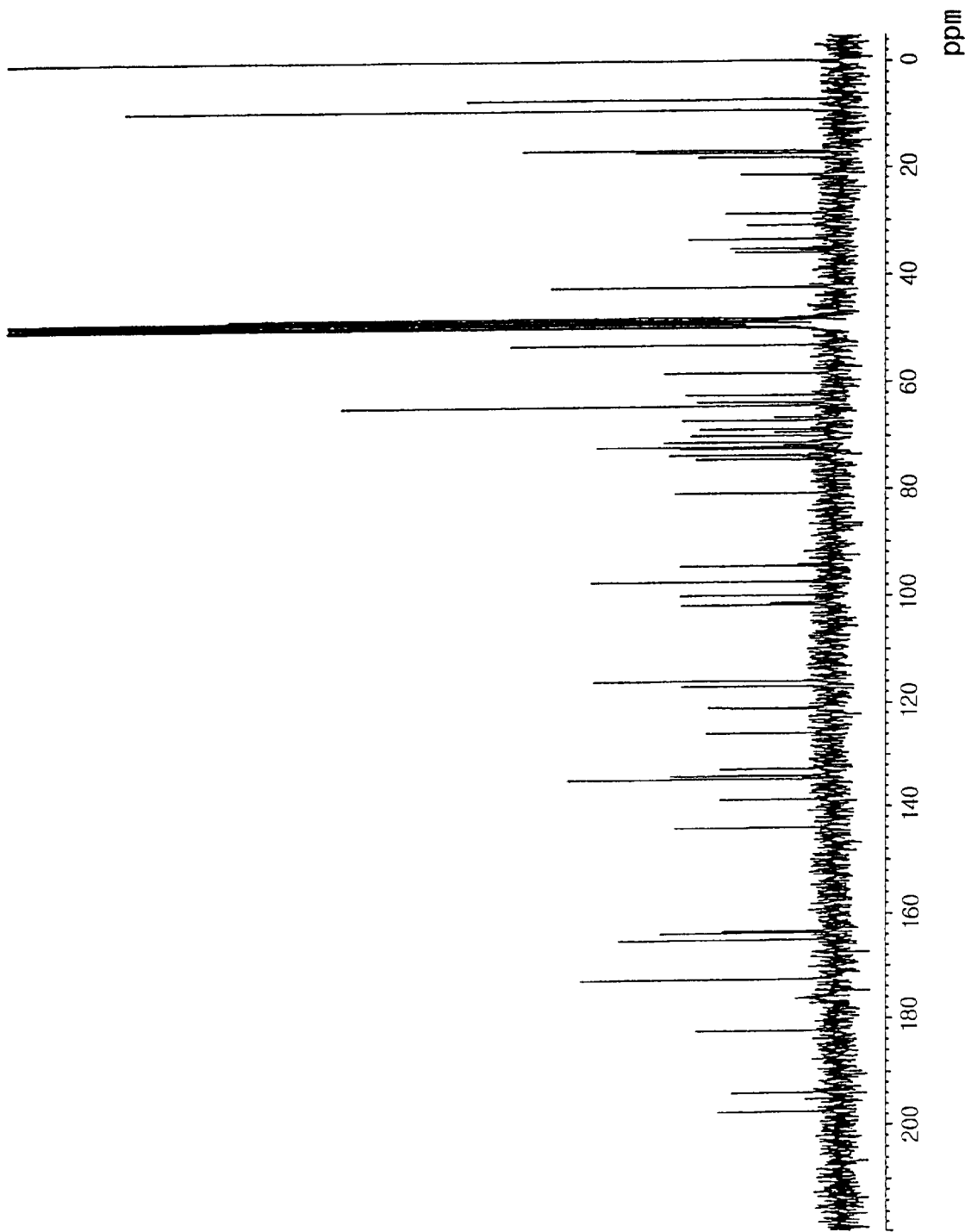
FIG. 8 displays the $^{13}$C-NMR spectrum of aclacinomycin X.

Based on the above results, aclacinomycin X was identified as a novel compound which has a rednose moiety instead of the L-cinerose A moiety of aclacinomycin A. The $^1$H- and $^{13}$C-NMR spectra of aclacinomycin X are shown in FIGS. 7 and 8, respectively.

EXAMPLE 8
Physicochemical Properties of Hybrid Aclacinomycins
1) Structure and Physicochemical properties of 11-hydroxy aclacinomycin A 11-hydroxy aclacinomycin A, a hybrid antibiotic, is a red powder having a melting point of 160°–162° C. and dissolves easily in MeOH or CHCL$_3$.

Aclacinomycin A showed UV spectrum peaks at 229, 258, 287 and 431 nm, but in the UV spectrum of 11-hydroxy aclacinomycin A, a bathochromic effect was observed and the absorption peaks have shifted to 234, 252, 294 and 491 nm. This effect is attributed to the introduction of a hydroxyl group into the carbon atom at position 11(hereinafter, referred to as C-11).

Figure 9:
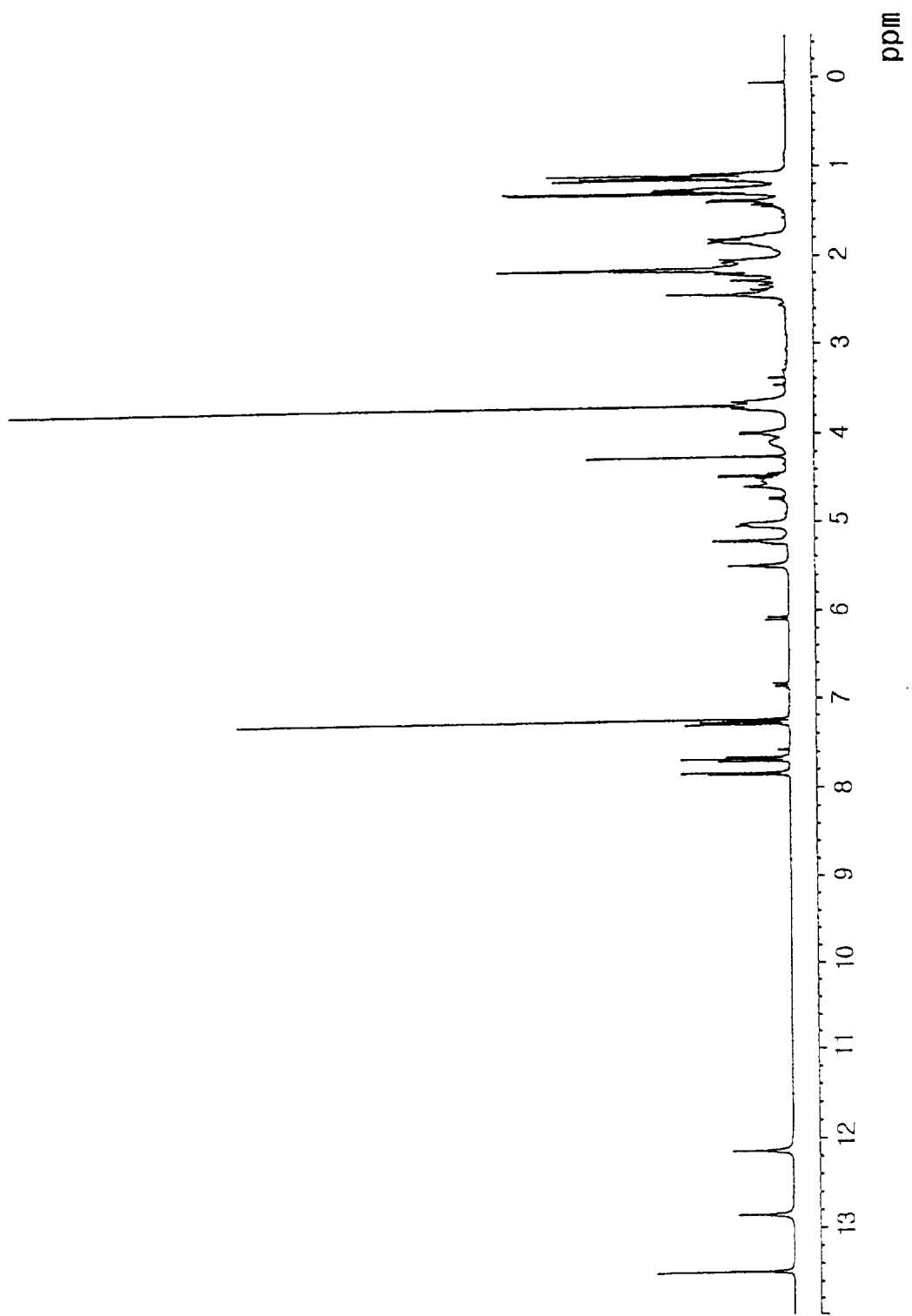
FIG. 9 exhibits the 1H-NMR spectrum of 11-hydroxy aclacinomycin A.
Figure 10:
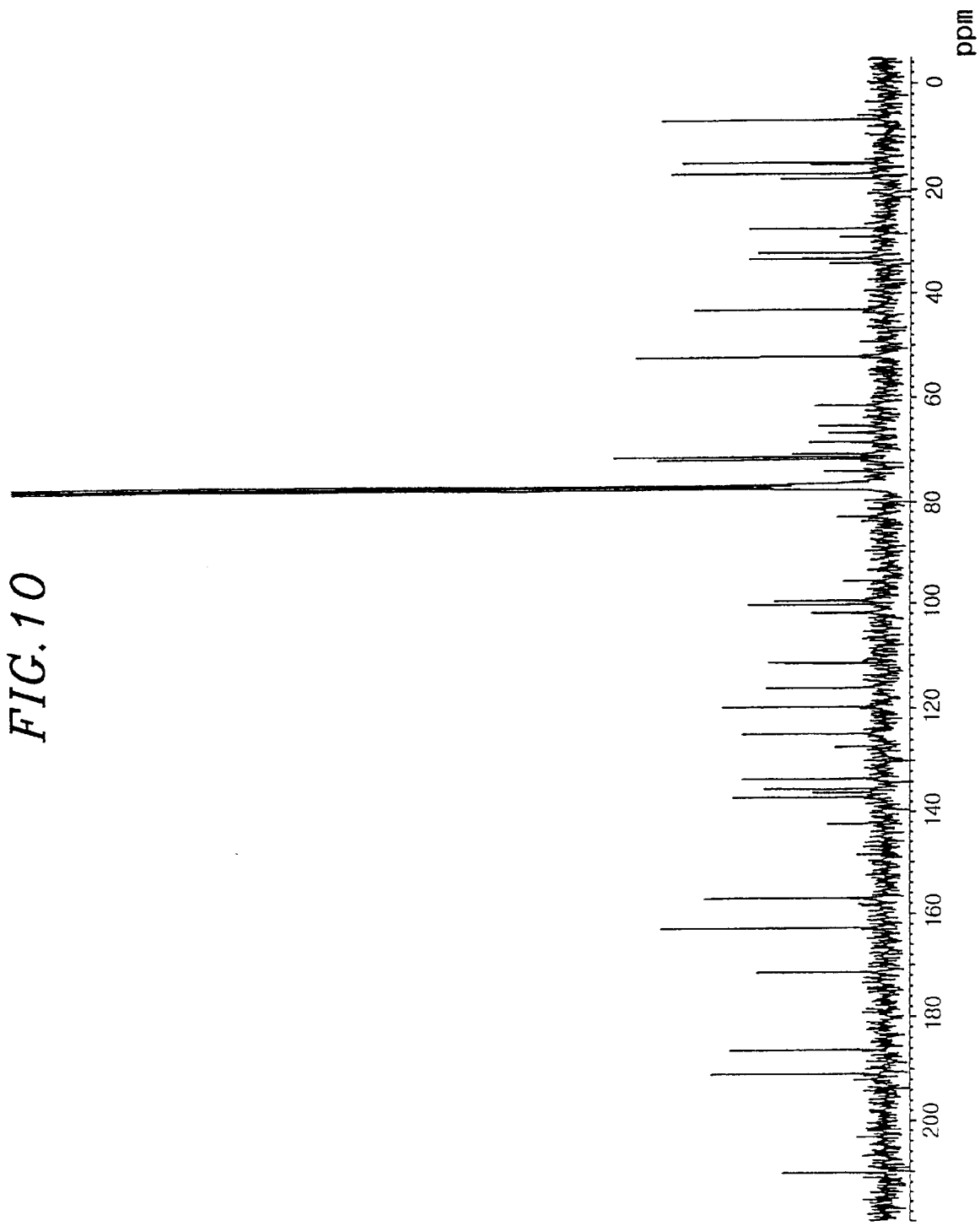
FIG. 10 illustrates the $^{13}$C-NMR spectrum of 11-hydroxy aclacinomycin A.

The $^1$H-NMR spectrum of 11-hydroxy aclacinomycin A was identical with that of aclacinomycin A, except for the absence of the singlet at 7.65 ppm which corresponds to the H atom attached to C-11. This demonstrated that C-11 is exactly the position of hydroxylation, which was also confirmed by the $^{13}$C-NMR spectrum of 11-hydroxy aclacinomycin A. Specifically, in the $^{13}$C-NMR spectrum of aclacinomycin A, C-11 was observed at 120.84 ppm, while it appeared downfield, i.e., at 156.91 ppm, in case of 11-hydroxy aclacinomycin A. The $^1$H-NMR and $^{13}$C-NMR spectra of 11-hydroxy aclacinomycin A are shown in FIGS. 9 and 10, respectively.

In the FAB-MS spectrum of 11-hydroxy aclacinomycin A, a molecular ion peak was observed at m/z 828(M+H$^+$), which is greater by 16 mass unit than that of aclacinomycin. An aglycon obtained by hydrolysing 11-hydroxy aclacinomycin A with 0.1N HCl showed, in TLC and HPLC analyses, an Rf value and a retention time which are identical with those of aclacinomycin A.

The results of the above instrumental analyses demonstrate that aklavinone C-11 hydroxylase gene was expressed in *S. galilaeus* ATCC 31133 to produce a hybrid antibiotic, i.e., 11-hydroxy aclacinomycin A, which is produced by introducing an OH group into C-11 of aclacinomycin A.

2) Structure and Physicochemical properties of 11-hydroxy aclacinomycin B 11-hydroxy aclacinomycin B, a hybrid antibiotic, is a red powder and it dissolves easily in MeOH and CHCl$_3$.

The UV spectrum of 11-hydroxy aclacinomycin B shows absorption peaks at 234, 254, 284 and 494 nm.

Figure 11:
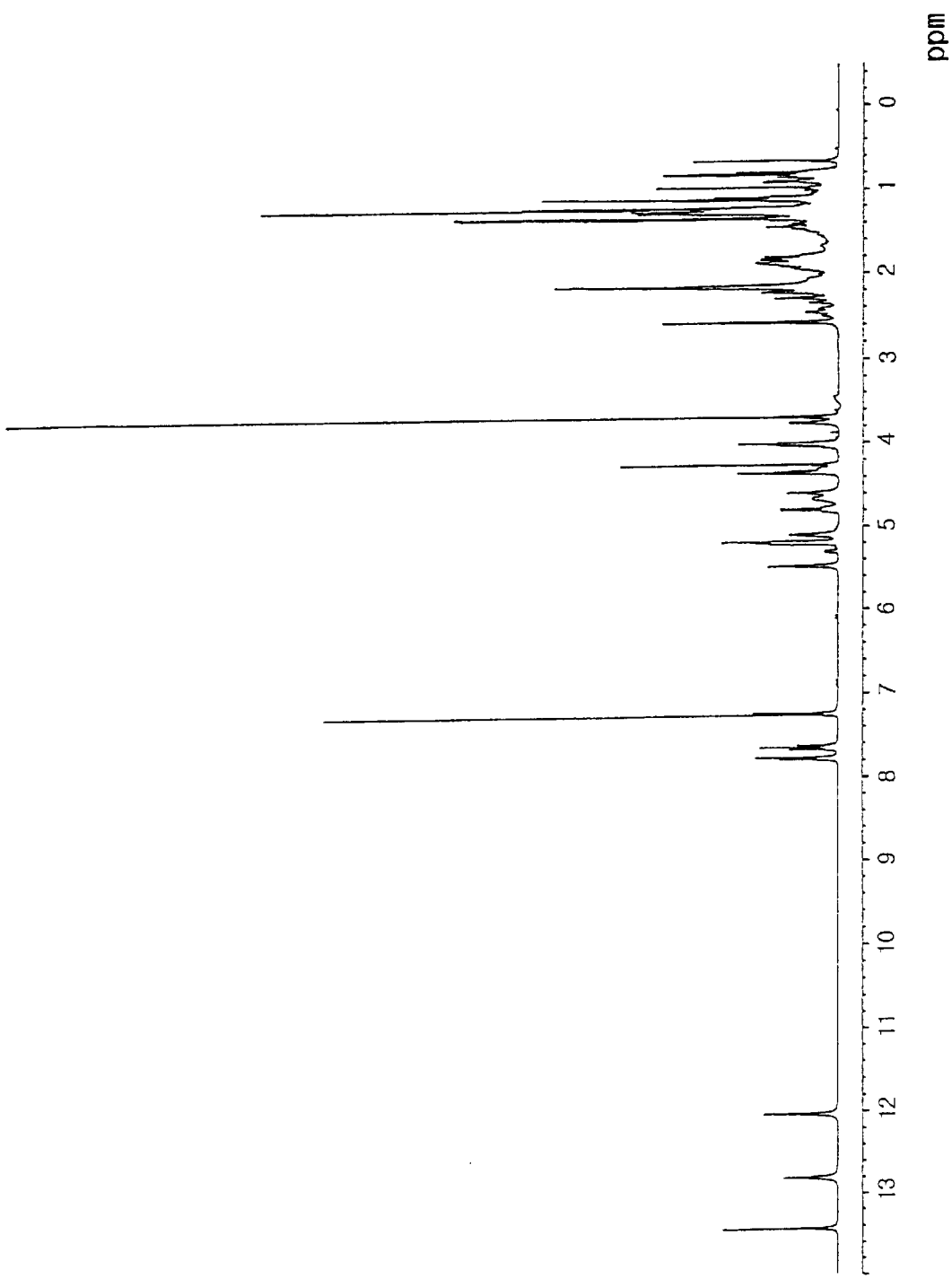
FIG. 11 shows the 1H-NMR spectrum of 11-hydroxy aclacinomycin B.
Figure 12:
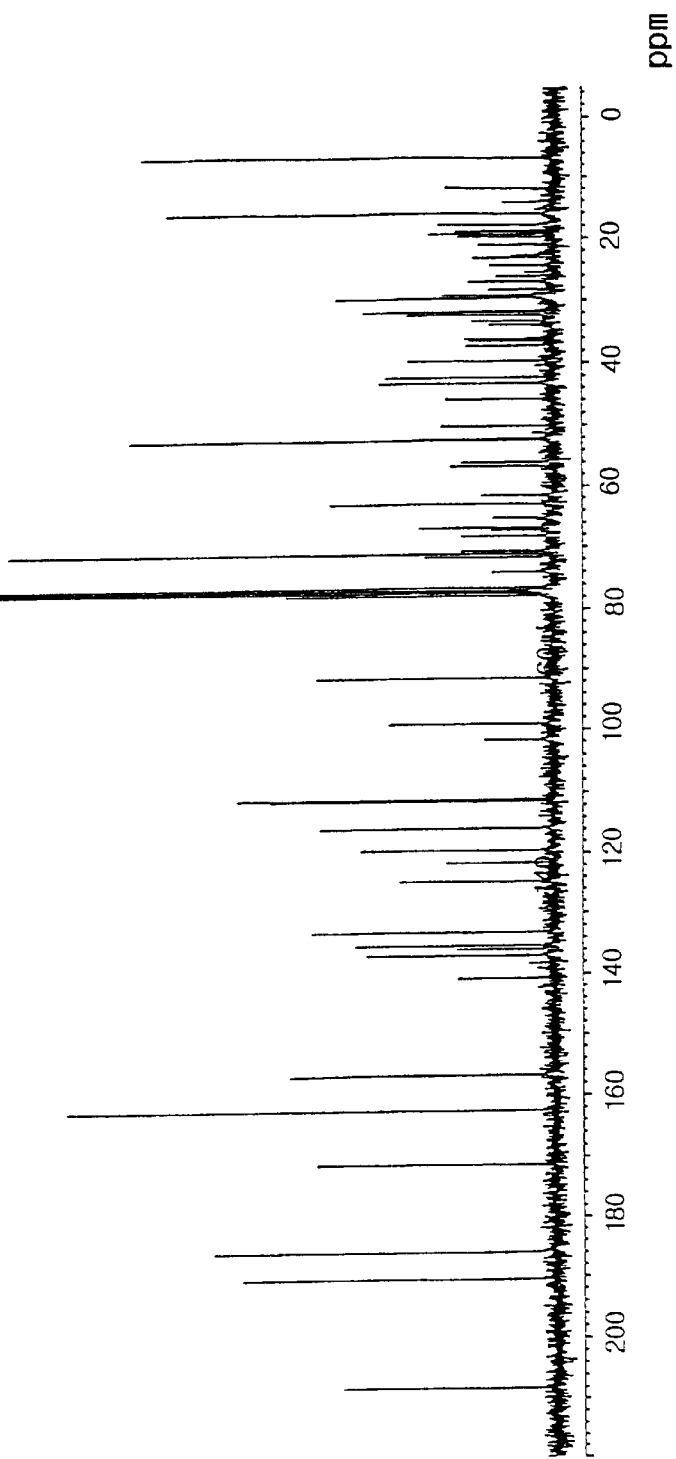
FIG. 12 depicts the $^{13}$C-NMR spectrum of 11-hydroxy aclacinomycin B.

$^1$H-NMR spectrum of the aglycon moiety of 11-hydroxy aclacinomycin B shows a chemical shift pattern identical with that of 11-hydroxy aclacinomycin A, while the chemical shift pattern of the bound sugar moiety is significantly different from that of 11-hydroxy aclacinomycin A. When the chemical shifts of the bound sugar moiety of 11-hydroxy aclacinomycin B are compared with those of aclacinomycin derivatives reported by Oki, T., et al.(*Antibiotics*, 32, 801–819(1979)), it is evident that 11-hydroxy aclacinomycin B has values identical with those of aclacinomycin B, in which C-l and C-2 of the third bound sugar, L-cinerulose B, are bonded, respectively, with C-4 and C-3 of the second bound sugar, 2- deoxy-L-fucose. In the $^3$C-NMR spectrum, 11-hydroxy aclacinomycin A shows C-4" at 82.68 ppm, C-1'" at 99.19 ppm, and C-2'" at 27.59 ppm, while 11-hydroxy aclacinomycin B showed C-4" at 66.82 ppm, C-1'" at 91.47 ppm, and C-2'" at 62.90 ppm. This result reveals that 11-hydroxy aclacinomycin B has three sugar moieties identical with those of aclacinomycin B. The $^1$H-NMR and $^{13}$C-NMR spectra of 11-hydroxy aclacinomycin B are shown in FIGS. 11 and 12, respectively.

3) Structure and Physicochemical properties of 11-hydroxy aclacinomycin X.

Figure 13:
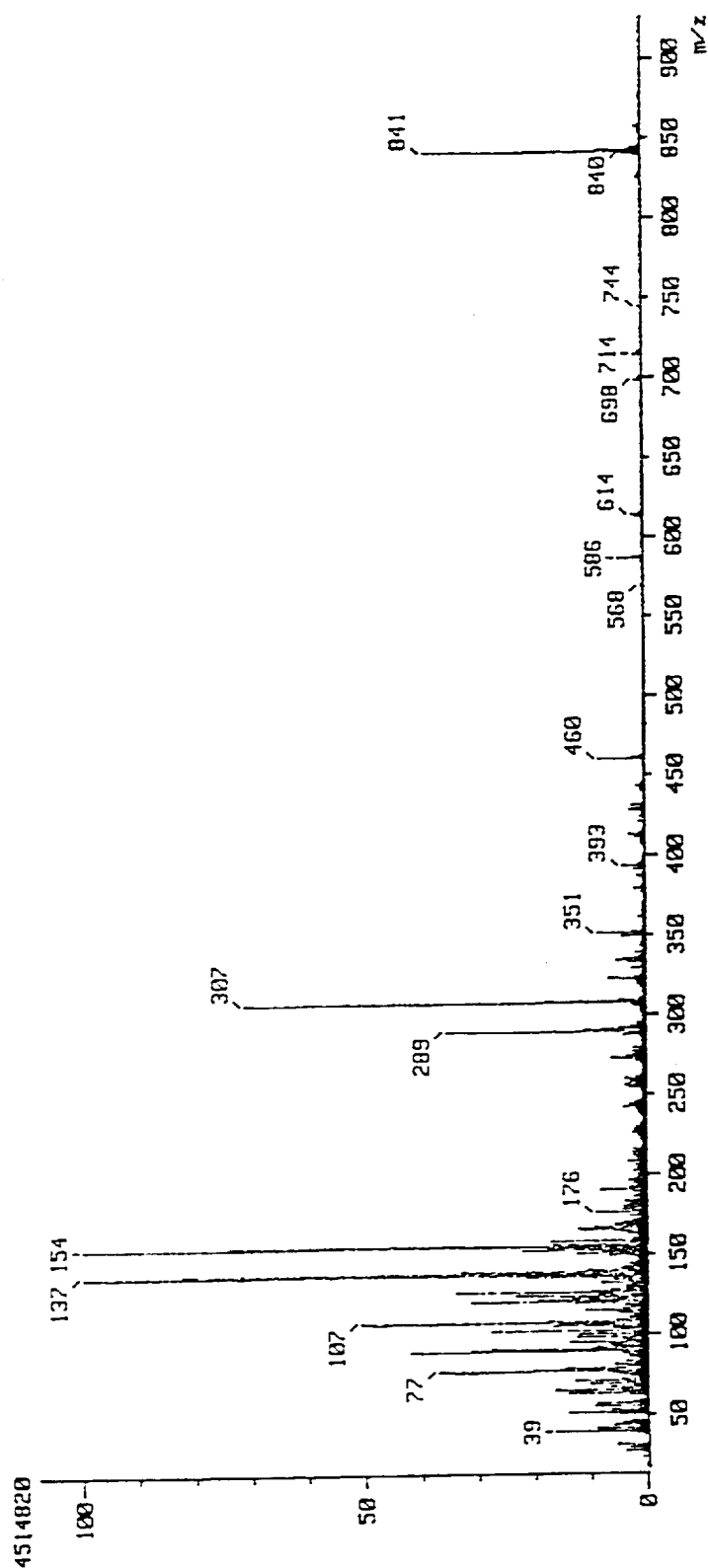
FIG. 13 displays the FAB-MS spectrum of 11-hydroxy aclacinomycin X.

11-Hydroxy aclacinomycin X is a red powder having a melting point of 184°–187° C. and it dissolves easily in MeOH or CHCl$_3$. UV spectrum of 11-hydroxy aclacinomycin X shows the absorption peaks at 234, 254, 284 and 492 nm, but, unlike aclacinomycin X, the absorption peak at 284 nm exhibits a hypsochromic effect. FAB-MS spectrum of 11-hydroxy aclacinomycin X shows a molecular ion peak at m/z 841(M+H$^+$) (FIG. 13).

In the $^1$H-NMR spectrum, the aglycon moiety as well as the rhodosamine and 2-deoxy-L-fucose moieties shows same chemical shifts as in 11-hydroxy aclacinomycin A. However, the chemical shift pattern of the third bound sugar is significantly different from that of 11-hydroxy aclacinomycin A, e.g. a new singlet is observed in the olefinic proton region at 5.34 ppm.

In the $^{13}$C-NMR spectrum, a quaternary carbon and a tertiary carbon appear at 159.46 and 95.29 ppm, respectively.

Figure 14:
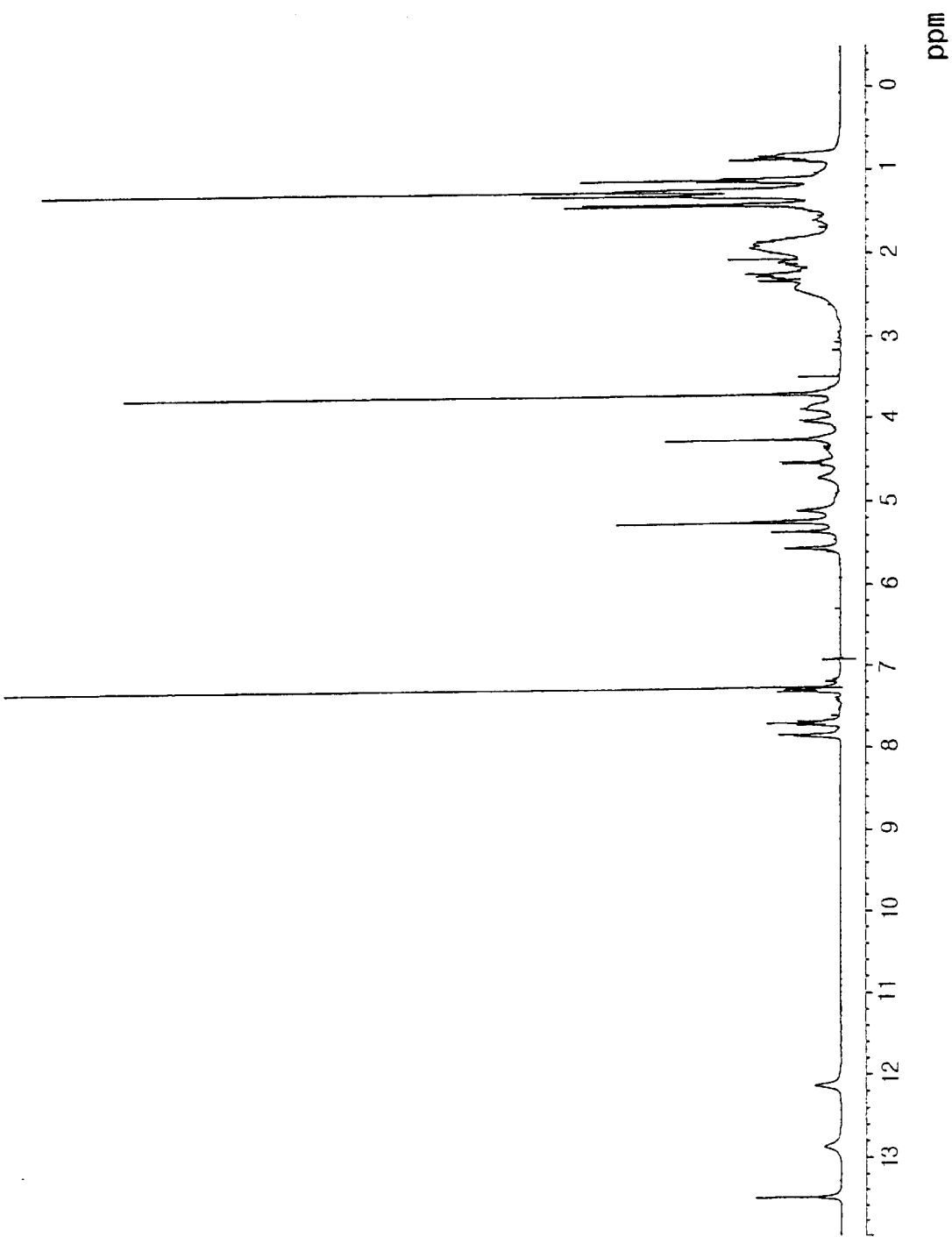
FIG. 14 exhibits the $^1$H-NMR spectrum of 11-hydroxy aclacinomycin X.
Figure 15:
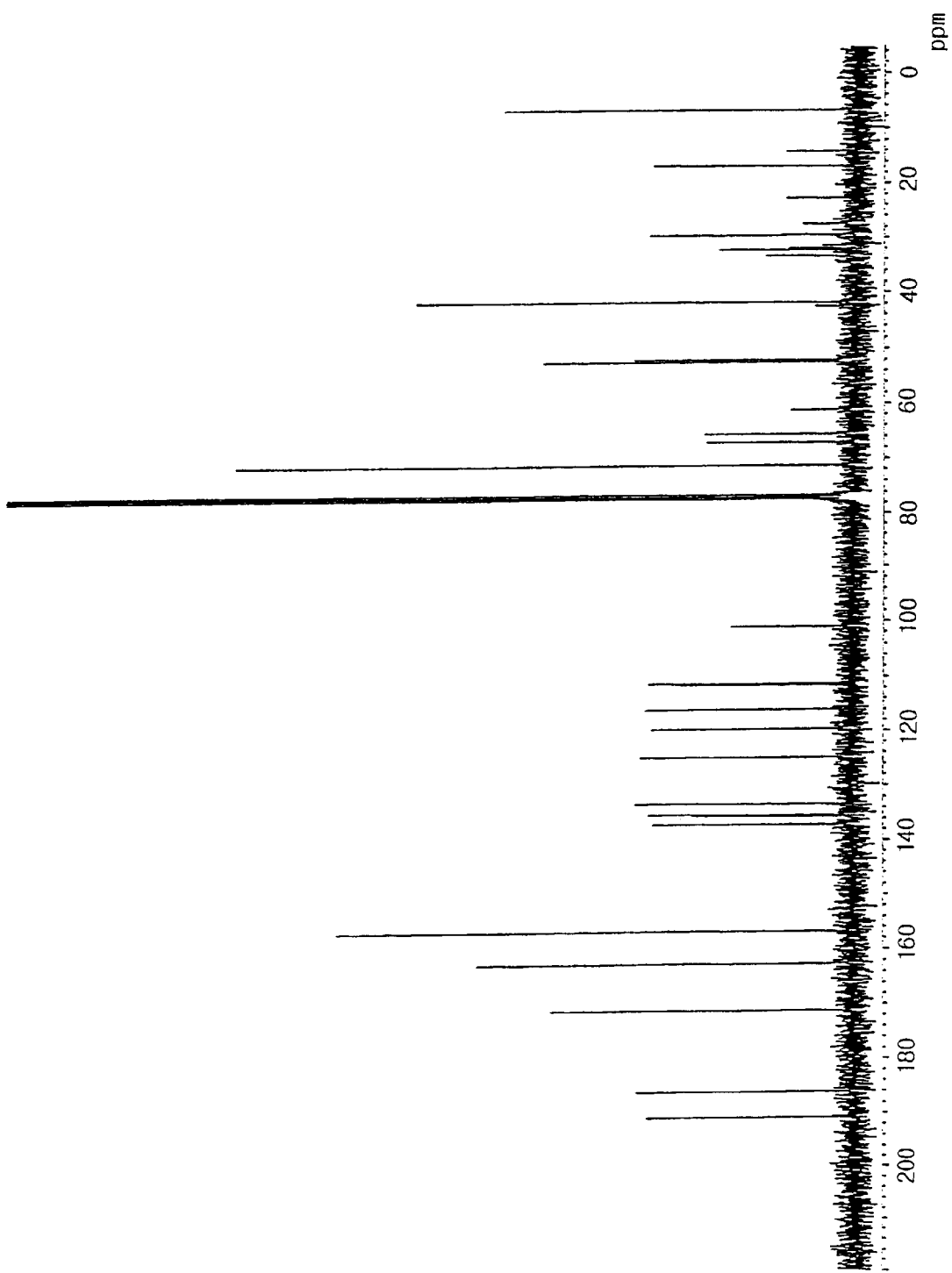
FIG. 15 illustrates the $^{13}$C-NMR spectrum of 11-hydroxy aclacinomycin X.

From the results of the above instrumental analyses, 11-hydroxy aclacinomycin X was identified as a novel compound which has a rednose moiety instead of the L-cinerose A moiety of 11-hydroxy aclacinomycin A. The 1H- and $^{13}$C-NMR spectra of the 11-hydroxy aclacinomycin X are shown in FIGS. 14 and 15, respectively.

4) Structure and Physicochemical properties of 11-hydroxy aclacinomycin T

11-Hydroxy aclacinomycin T is a red powder having a melting point of 145°–147° C. and it dissolves easily in MeOH or CHCl$_3$. UV spectrum of 11-hydroxy aclacinomycin T shows absorption peaks at 234, 254, 292 and 492 nm.

Figure 16:
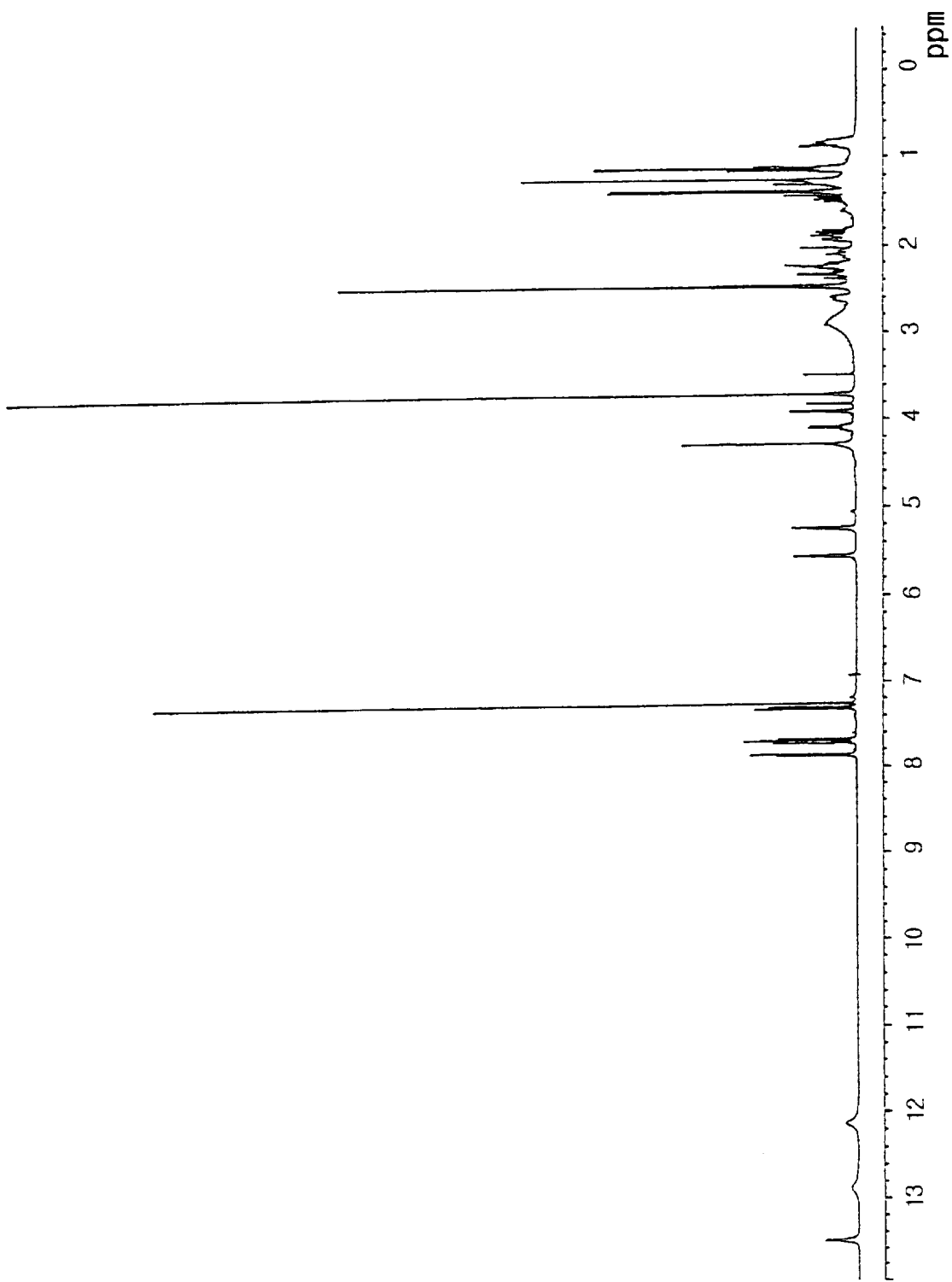
FIG. 16 shows the $^1$H-NMR spectrum of 11-hydroxy aclacinomycin T.

$^1$H-NMR spectrum (FIG.16) of 11-hydroxy aclacinomycin T is similar to that of 11-hydroxy aclacinomycin A, except that only two hydrogen atoms, i.e., H-1'and H-7, are observed at the position of anomeric proton. From this result, it is presumed that 11-hydroxy aclacinomycin T includes only one sugar moiety.

Figure 17:
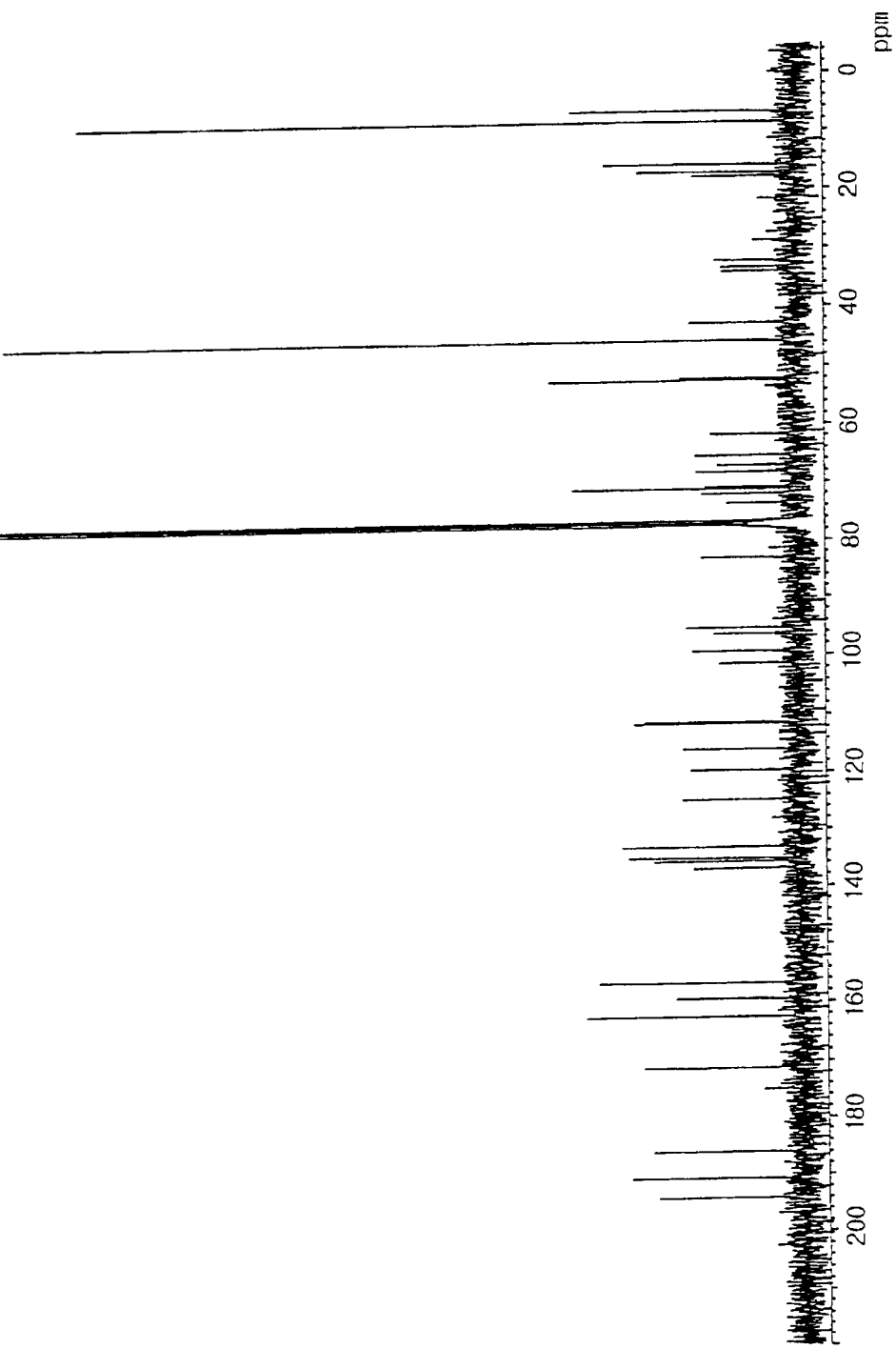
FIG. 17 depicts the $^{13}$C-NMR spectrum of 11-hydroxy aclacinomycin T.

EI-MS of 11-hydroxy aclacinomycin T reveals a molecular ion peak at m/z 585. Analysis of the $^{13}$C-NMR spectrum (FIG.17) showed that the subject compound is 11-hydroxy aclacinomycin T.

EXAMPLE 9
Anticancer Activity of Anthracyclines

The anticancer activities of aclacinomycin X, 11-hydroxy aclacinomycin X and 11-hydroxy aclacinomycin A were determined by using a reduced human cancer cell line panel(supplier: National Cancer Institute, U.S.A.) in accordance with the method of National Cancer Institute, U.S.A. (Monks, A., et al.,*J. Natl. Cancer Inst.*, 83, 757–766(1991)), and the results are shown in Table I.

TABLE I

Anti-Cancer Activity of Anthracyclines

| Panel/Cell Line | Aclacinomycin X | 11-Hydroxy aclacinomycin X | 11-Hydroxy aclacinomycin A |
|---|---|---|---|
| Leukemia/ | | | |
| HL-60 TB | −4.51 | −6.63 | <−8.00 |
| K-562 | −4.22 | −5.12 | −5.75 |
| Non-Small Cell Lung Cancer/ | | | |
| A-549 | −5.39 | −4.67 | −4.61 |
| EKVX | −4.73 | −6.01 | −6.59 |
| Colon Cancer/ | | | |
| HCC-2298 | −6.72 | — | <−8.00 |
| HT29 | −4.51 | −4.32 | −4.89 |
| CNS Cancer/ | | | |
| SF-268 | −4.95 | >−4.00 | −4.10 |
| U251 | −4.74 | >−4.00 | −4.25 |
| Melanoma/ | | | |
| MALME-3M | −6.25 | −7.27 | −7.17 |
| SK-MEL-2 | −7.28 | <−8.00 | <−8.00 |
| Ovarian Cancer/ | | | |
| OVCAR-3 | >−4.00 | >−4.00 | −4.14 |
| SK-OV-3 | >−4.00 | — | −4.41 |
| Renal Cancer/ | | | |
| 786-0 | −4.74 | −5.34 | −5.08 |
| UO-31 | −4.58 | −4.81 | −4.72 |
| Prostate Cancer/ | | | |
| PC-3 | −5.08 | −5.17 | −4.84 |
| DU-145 | −4.52 | −4.38 | −4.61 |
| Breast Cancer/ | | | |
| MCF7 | −4.36 | −4.51 | −4.60 |
| MDA-N | >−4.00 | >−4.00 | −4.00 |

As can be seen from the result of Table I, all of the tested compounds showed high anticancer activities, particularly against melanoma. Aclacinomycin X showed selective anticancer activities against colon cancer, melanoma and breast cancer cell lines. 11-hydroxy aclacinomycin X showed an anticancer activity pattern similar to that of aclacinomycin X, but its anticancer activities were higher than aclacinomycin X against leukemia, melanoma and breast cancer cell lines. It can thus be shown that 11-hydroxy anthracyclines have higher anticancer activities than anthracyclines which do not carry a 11-hydroxy group. However, 11-hydroxy anthracycline A still showed a high anticancer activity against leukemia, colon cancer and melanoma cell lines.

While the invention has been described with respect to the above specific embodiments, it should be recognized that various modifications and changes may be made to the invention by those skilled in the art which also fall within the scope of the invention as defined by the appended claims.

What is claimed is:

1. An isolated aklavinone C-11 hydroxylase having SEQ ID NO :3.

2. An isolated polynucleotide sequence encoding aklavinone C-11hydroxylase having SEQ ID NO:4.

3. A vector comprising the polynucleotide sequence of claim 2.

4. The vector of claim 3, wherein the vector is plasmid pMC213(KCTC 0162BP).

5. A *Streptomyces galilaeous* strain transformed with the vector of claim 3.

6. The *Streptomyces galilaeous* strain ATCC 31133 transformed with plasmid pMC213.

7. A process for the preparation of an 11-hydroxy aclacinomycin comprising:

transforming *Streptomyces galilaeous* ATCC 31133 with plasmid pMC213 ;

culturing the *Streptomyces galilaeous* strain ATCC 31133 transformed with the plasmid pMC213 for a time and under suitable conditions to produce said aclacinomycin and recovering said aclacinomycin.

8. The process of claim 7, wherein said 11-hydroxy aclacinomycin is 11-hydroxy aclacinomycin A, 11-hydroxy aclacinomycin B, 11-hydroxy aclacinomycin X or 11-hydroxy aclacinomycin T having the structures of:

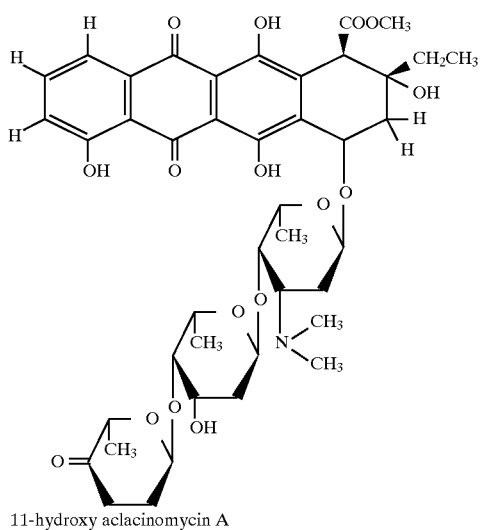
11-hydroxy aclacinomycin A
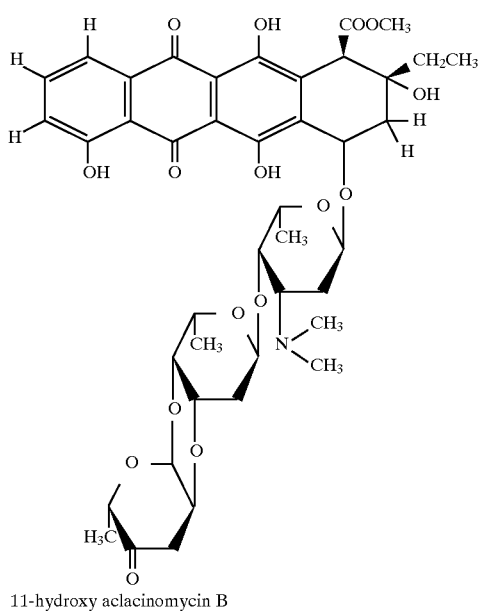
11-hydroxy aclacinomycin B
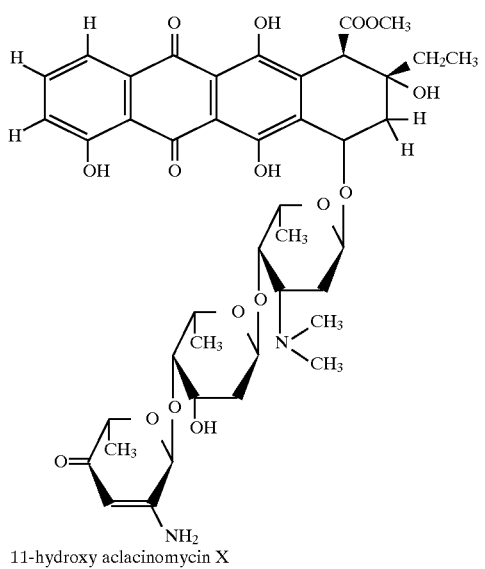
11-hydroxy aclacinomycin X
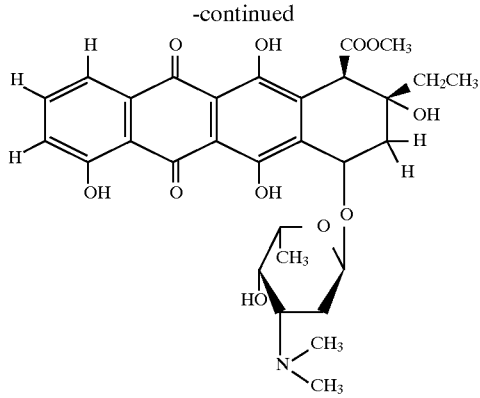
11-hydroxy aclacinomycin T.
9. An aclacinomycin compound X of the formula.
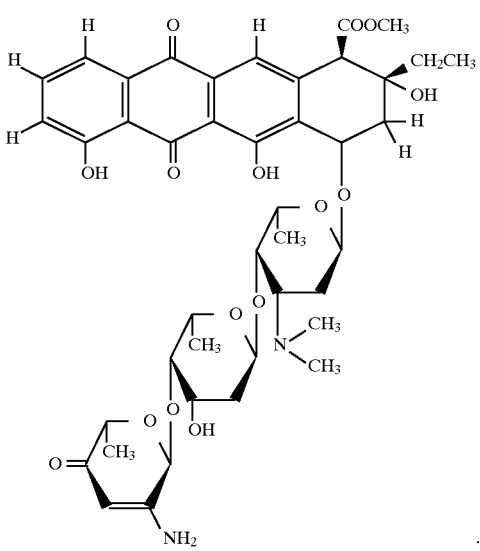
10. An aclacinomycin compound X of the formula.
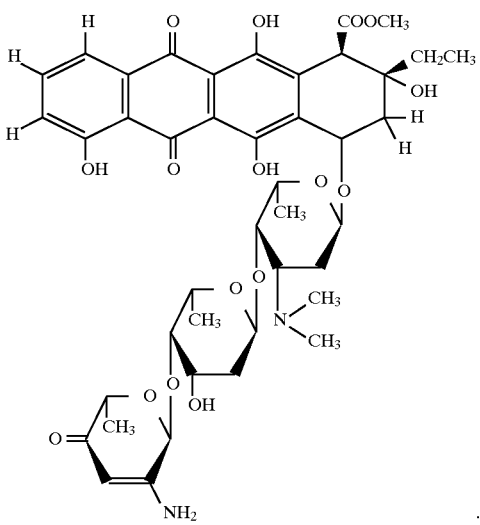
* * * * *